(12) United States Patent
Devasthale et al.

(10) Patent No.: US 6,673,815 B2
(45) Date of Patent: Jan. 6, 2004

(54) SUBSTITUTED ACID DERIVATIVES USEFUL AS ANTIDIABETIC AND ANTIOBESITY AGENTS AND METHOD

(75) Inventors: Pratik Devasthale, Plainsboro, NJ (US); Yoon T. Jeon, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/289,053

(22) Filed: Nov. 6, 2002

(65) Prior Publication Data

US 2003/0130306 A1 Jul. 10, 2003

Related U.S. Application Data

(60) Provisional application No. 60/333,022, filed on Nov. 6, 2001.

(51) Int. Cl.[7] ............... C07D 263/52; A61K 31/445
(52) U.S. Cl. ............... 514/325; 514/375; 546/203; 548/217; 548/253
(58) Field of Search ............... 514/375, 325; 548/217, 253; 546/203

(56) References Cited

FOREIGN PATENT DOCUMENTS

JP        63104969     *  10/1986

OTHER PUBLICATIONS

Fujiwara, et al, Life Sciences (2000), 67(20), 2405–2416.*

Thacher, at al, Current Pharmaceutical Design, 2000, 6, 25–58.*

* cited by examiner

Primary Examiner—Joseph K. McKane
Assistant Examiner—Andrea D. Small
(74) Attorney, Agent, or Firm—Burton Rodney

(57) ABSTRACT

Compounds are provided which have the structure

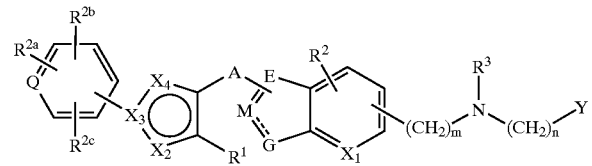

wherein Q is C or N, $X_1$ is CH or N and, A, E, M, G, $X_2$, $X_3$, $X_4$, $R^1$, $R^2$, $R^{2a}$, $R^{2b}$, $R^{2c}$, $R^3$, Y, x, m, and n are as defined herein, which compounds are useful as antidiabetic, hypolipidemic, and antiobesity agents.

35 Claims, No Drawings

SUBSTITUTED ACID DERIVATIVES USEFUL AS ANTIDIABETIC AND ANTIOBESITY AGENTS AND METHOD

This application claims priority from U.S. Provisional Application No. 60/333,022 filed Nov. 6, 2001 which is incorporated herein by reference.

FIELD OF THE INVENTION

The present invention relates to novel substituted acid derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted acid derivatives alone or in combination with another antidiabetic agent and/or a hypolipidemic agent and/or other therapeutic agents.

DESCRIPTION OF THE INVENTION

In accordance with the present invention, substituted acid derivatives are provided which have the structure I

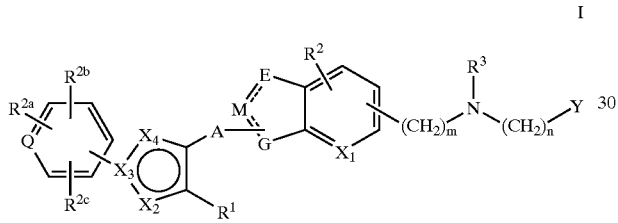

wherein
m is 0, 1 or 2; n is 0, 1 or 2;
Q is C or N;
A is $(CH_2)_x$ where x is 1 to 5; or A is $(CH_2)_x^1$ where $x^1$ is 2 to 5, with an alkenyl bond or an alkynyl bond embedded anywhere in the chain; or A is $—(CH_2)_x^2—O—(CH_2)_x^3—$ where $x^2$ is 0 to 5 and $x^3$ is 0 to 5, provided that at least one of $x^2$ and $x^3$ is other than 0;
$X_1$ is CH or N;
$X_2$ is $CR^a$, $NR^b$, O or S;
$X_3$ is $CR^c$ or $NR^d$;
$X_4$ is $CR^e$, $NR^f$, O or S, wherein $R^a$, $R^c$ and $R^e$ are the same or different and are independently selected from a single bond, H, alkyl, alkoxy, aryl, cycloalkyl, amino or substituted amino, and $R^b$, $R^d$ and $R^f$ are the same or different and are independently selected from a single bond, H, alkyl, alkoxy, aryl, heteroaryl, cycloalkyl or cycloheteroalkyl, provided that at least one of $X_2$, $X_3$ and $X_4$ is

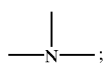

E is O, S, $NR^g$ or $CR^h$;
M is $NR^i$ or $CR^j$;
G is O, S, $NR^k$ or $CR^l$, wherein $R^g$, $R^i$ and $R^k$ are the same of different and are independently selected from a single bond, H, alkyl, aryl, heteroaryl, cycloalkyl or cycloheteroalkyl, and $R^h$, $R^j$ and $R^l$ are the same or different and are independently selected from a single bond, H, alkyl, alkoxy, aryl, cycloalkyl, amino or substituted amino;
provided that at least one of E, M and G is other than CH or C;

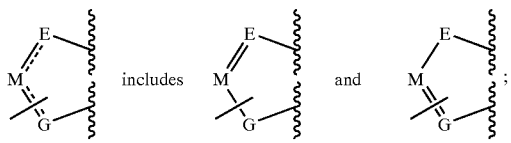

and where E, M and G are each

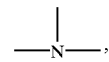

then A is other than $—CH_2—O—$; and where in each of $X_1$ through $X_4$ as defined above, C may include CH;
$R^1$ is H or alkyl;
$R^2$ is H, alkyl, alkoxy, halogen, amino or substituted amino;
$R^{2a}$, $R^{2b}$ and $R^{2c}$ may be the same or different and are selected from H, alkyl, alkoxy, halogen, amino or substituted amino;
$R^3$ is selected from aryloxycarbonyl, alkyloxycarbonyl, alkynyloxycarbonyl, alkenyloxycarbonyl, alkyl(halo)aryloxycarbonyl, alkyloxy(halo)aryloxycarbonyl, cycloalkylaryloxycarbonyl, cycloalkyloxyaryloxycarbonyl, alkylcarbonylamino, arylcarbonylamino, heteroarylcarbonylamino, alkoxycarbonylamino, aryloxycarbonylamino, heteroaryloxycarbonylamino, alkylsulfonyl, alkenylsulfonyl, heteroaryloxycarbonyl, cycloheteroalkyloxycarbonyl, heteroarylalkenyl, hydroxyalkyl, alkoxy, alkoxyaryloxycarbonyl, arylalkyloxycarbonyl, alkylaryloxycarbonyl, haloalkoxyaryloxycarbonyl, alkoxycarbonylaryloxycarbonyl, aryloxyaryloxycarbonyl, heteroaryloxyarylalkyl, aryloxyarylalkyloxycarbonyl, arylalkenyloxycarbonyl, aryloxyalkyloxycarbonyl, arylalkylsulfonyl, arylthiocarbonyl, arylalkenylsulfonyl, heteroarylsulfonyl, arylsulfonyl, heteroarylalkoxycarbonyl, heteroarylalkyloxyarylalkyl, arylalkenylarylalkyl, heteroaryloxyarylalkyl, arylalkenylheteroarylalkyl, or polyhaloalkylaryloxycarbonyl;
Y is $CO_2R^4$ (where $R^4$ is H or alkyl, or a prodrug ester) or Y is a C-linked 1-tetrazole, a phosphinic acid of the structure $P(O)(OR^{4a})R^5$ ($R^5$ is alkyl or aryl) or a phosphonic acid of the structure $P(O)(OR^{4a})_2$ (where $R^{4a}$ is H or a prodrug ester);
$(CH_2)_x$, $(CH_2)_x^1$, $(CH_2)_x^2$, $(CH_2)_x^3$, $(CH_2)_m$, and $(CH_2)_n$ may be optionally substituted with 1, 2 or 3 substituents;
including all stereoisomers thereof, prodrug esters thereof, and pharmaceutically acceptable salts thereof.

Preferred compounds of formula I of the invention have the structure

Ia

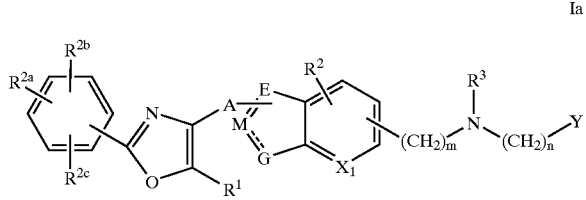

More preferred are compounds of formula I of the invention having the structure

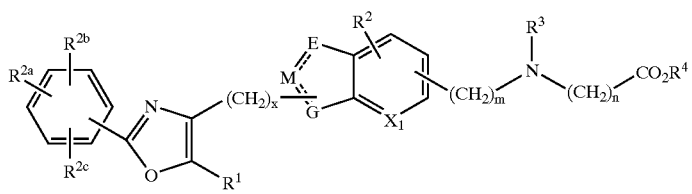

Ib

Still more preferred are compounds of formula I of the invention having the structures

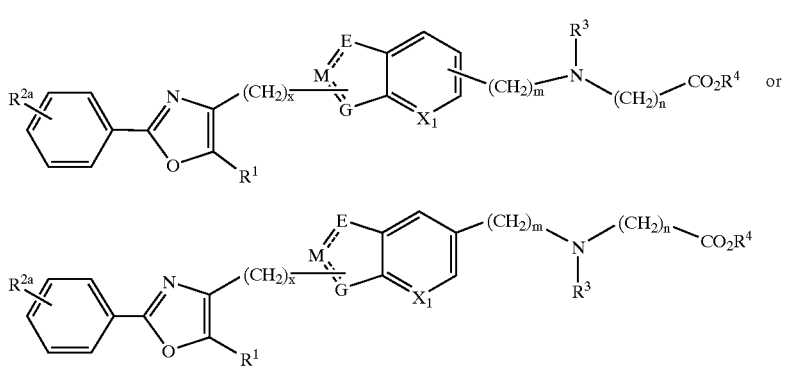

Ic or

Id

In the above compounds, it is preferred that $R^{2a}$ is H or alkoxy, but more preferably H, $(CH_2)_x$ is $CH_2$, $(CH_2)_2$, $(CH_2)_3$, or

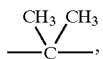

$(CH_2)_m$ is $CH_2$, or

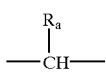

(where $R_a$ is alkyl such as methyl, or alkenyl such as

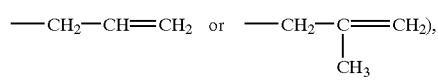

$(CH_2)_n$ is $CH_2$, $R^1$ is lower alkyl, preferably $CH_3$, $R^2$ is H, $R^{2a}$ is H, $R^4$ is H, $X_1$ is CH, and $R^3$ is arylalkyloxycarbonyl, aryloxycarbonyl, haloaryloxycarbonyl, alkoxyaryloxycarbonyl, alkylaryloxycarbonyl, aryloxyaryloxycarbonyl, heteroaryloxyarylalkyl, heteroaryloxycarbonyl, arylalkenyloxycarbonyl, cycloalkylaryloxycarbonyl, cycloalkyloxyaryloxycarbonyl, arylalkylsulfonyl, arylalkenylsulfonyl, arylthiocarbonyl, cycloheteroalkylalkyloxycarbonyl, cycloheteroalkyloxycarbonyl, or polyhaloalkyl-aryloxycarbonyl, wherein the above preferred groups may be optionally substituted, such as

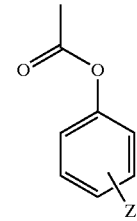

where Z is alkoxy, alkyl or halo.

Preferred examples of the group

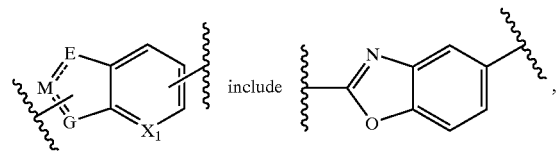

include

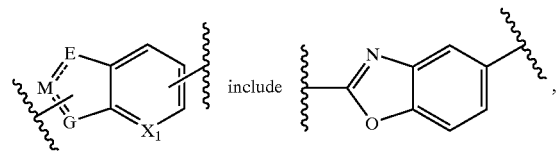

,

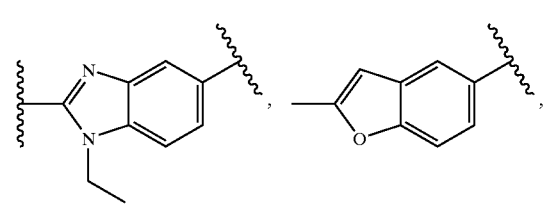

,

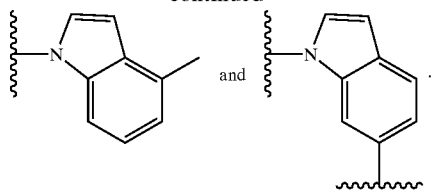 and
More preferred are compounds of formula I of the invention having the structure
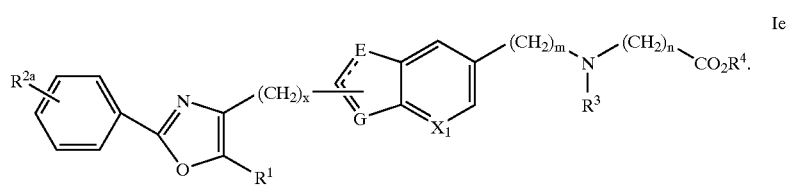
Preferred compounds of the invention include the following:
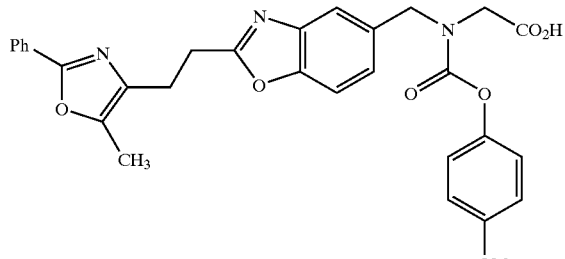
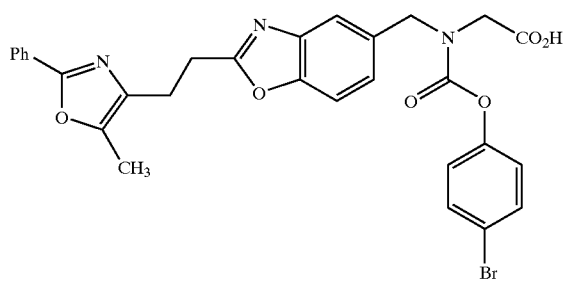
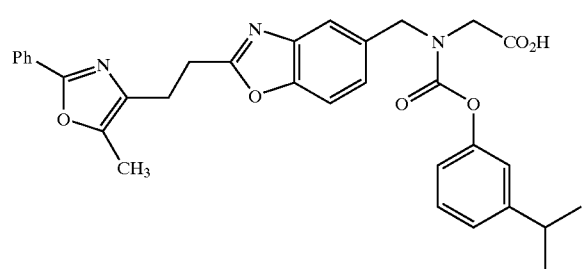
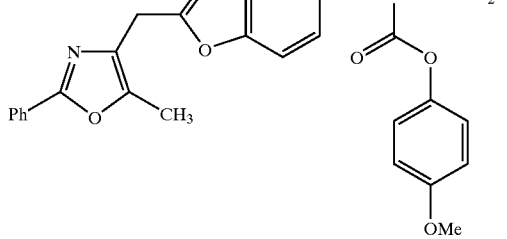
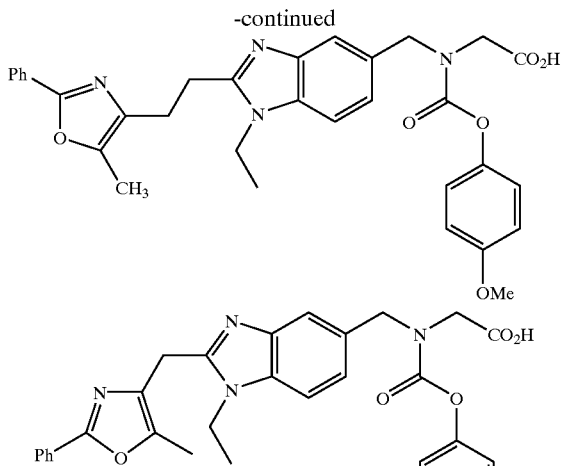
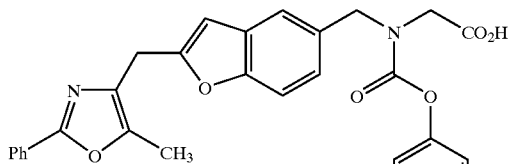
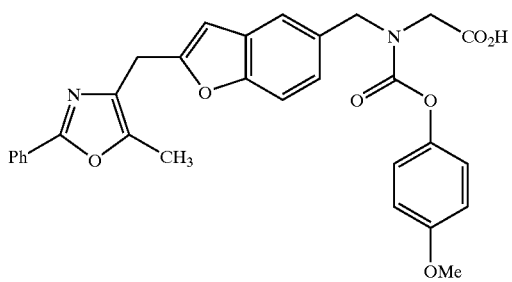

-continued

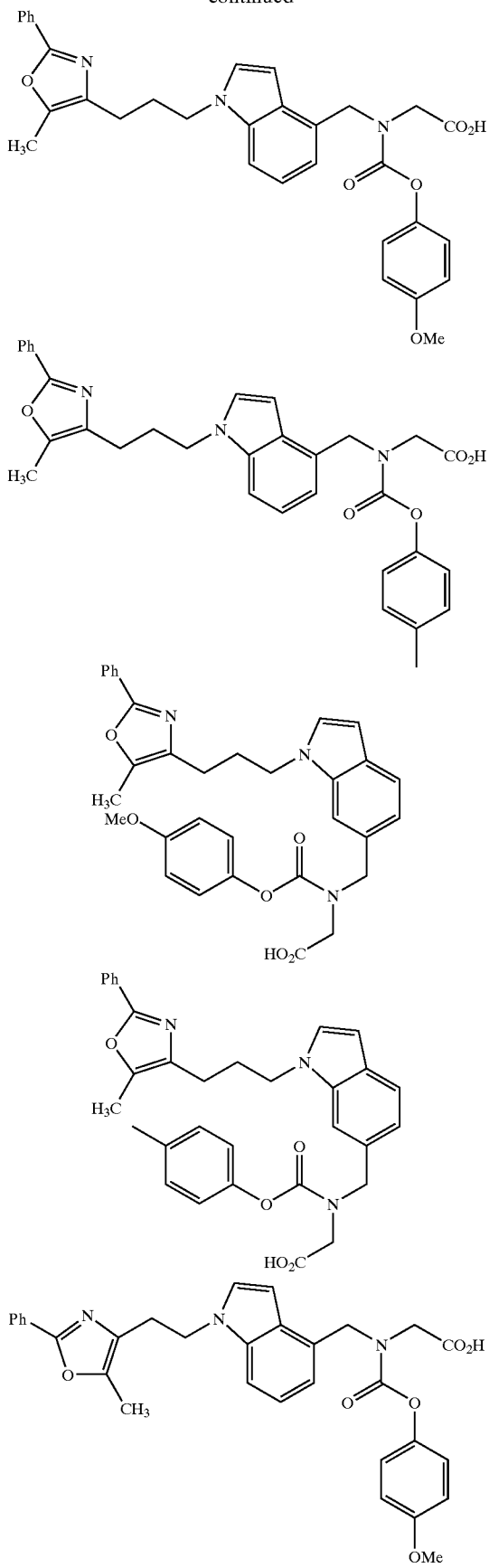

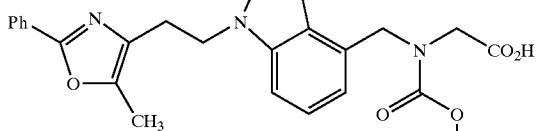
-continued

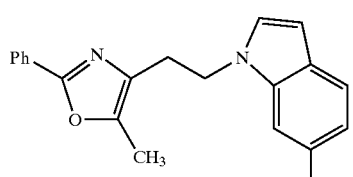

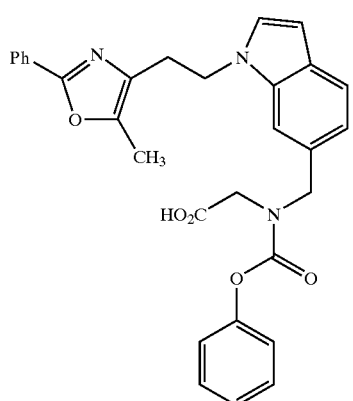

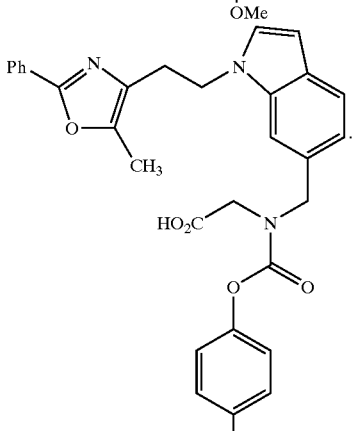

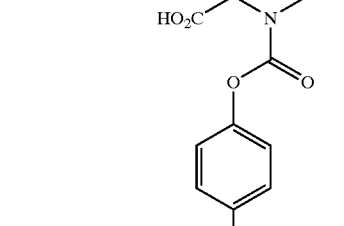

In addition, in accordance with the present invention, a method is provided for treating diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis and related diseases wherein a therapeutically effective amount of a compound of structure I is administered to a human patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis, and proliferative diseases such as psoriasis, wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a human patient in need of treatment.

In the above method of the invention, the compound of structure I will be employed in a weight ratio to the antidiabetic agent (depending upon its mode of operation) within the range from about 0.01:1 to about 100:1, preferably from about 0.5:1 to about 10:1.

DETAILED DESCRIPTION OF THE INVENTION

The conditions, diseases, and maladies collectively referenced to as "Syndrome X" or Dysmetabolic Syndrome (as detailed in Johanson, *J. Clin. Endocrinol. Metab.*, 1997, 82, 727–734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, Greene, T. W. and Wuts, P. G. M., Protecting Groups in Organic Synthesis, 3$^{rd}$ Edition, 1999 [Wiley]).

Scheme 1 describes a general synthesis of carbamate acids IA with a benzoxazole core described in this invention. An alcohol 1 (of which the most preferred is 2-phenyl-5-methyl-oxazole-4-ethanol) is converted to the corresponding nitrile using literature procedures (Aesa, M. et al. Synth. Commun. 1996, 26(5), 909–914) and treated with ethanolic HCl to yield an, imidate which is condensed with aminophenol 2 (preferably 3-amino-4-hydroxybenzoic acid methyl ester or 4-amino-3-hydroxybenzoic acid methyl ester) under reported conditions (P. D. Edwards et al. J. Med. Chem. 1995, 38, 3972–3982) to afford the corresponding benzoxazoles 3. The methyl ester is transformed, using standard methodology, to aldehyde 4 (Scheme 1). The resulting aldehyde 4 is then subjected to reductive amination using procedures known in the literature (e.g. Abdel-Magid et al, *J. Org. Chem.* 1996, 61, 3849) with an α-amino ester hydrochloride 5. PG in Scheme 1 denotes a preferred carboxylic acid protecting group, such as a methyl or tert-butyl ester. The resulting secondary amino-ester 6 is then treated with halide 7 such as $R^3Cl$, preferably a chloroformate, to afford an ester. Final deprotection of the carboxylic acid ester under standard conditions known in the literature (Greene et al supra) utilizing basic conditions (for methyl esters) or acidic conditions (for tert-butyl esters) then furnishes the desired amino acid product IA.

Scheme 2 describes a general synthesis of acid IB with a benzimidazole core. Fluoronitroarene 8 (preferably 4-amino-3-nitrobenzoic acid methyl ester) is reacted with an appropriate amine ($R^aNH_2$) (where $R^a$ is H, alkyl, aryl, cycloalkyl, heteroaryl or cyclohetroalkyl) to yield nitroaniline ester 9. Ester 9 is transformed, using standard methodology, to aldehyde 10 (Scheme 2). The resulting aldehyde 10 is then subjected to reductive amination as described above for the synthesis of IA in Scheme I. The resulting secondary amino-ester is then treated with a variety of halides 7, preferably chloroformates, and subjected to hydrogenation to afford 2-aminoaniline 11. The diamine 11 is coupled under EDAC-(1-ethyl-3-(3-dimethylaminopropyl) carbodiimide, EDCI or WSC) or BOP-mediated conditions (B. Castro et al, Tetrahedron Lett., 1975, 1219) to afford, after deprotection, the desired benzimidazoles IB.

Scheme 3 describes a general synthesis of carbamate acid IC with a benzofuran core. Iodophenol 12 (preferably 3-iodo-4-hydroxybenzaldehyde) is coupled under Pd(II) and $Cu_2O$-catalyzed conditions (B. Hulin et al. J. Med. Chem. 1996, 39, 3897–3907) with an appropriate acetylene 13 (the preferred acetylene being 5-phenyl-2-methyl-oxazol-4-yl-methylacetylene) to afford benzofuran 14. Following the protocol described above for Scheme I, aldehyde 14 is transformed to acid IC.

Indole-containing acid ID is synthesized from appropriately substituted indole 16 as described in Scheme 4. Indole ester 16 (preferably indole 4-carboxylic acid ester or indole 6-carboxylic acid ester) is reacted with primary mesylate 15 (most preferred mesylate being derived from 2-phenyl-5-methyl-oxazole-4-ethanol or 2-phenyl-5-methyl-oxazole-4-propanol) in the presence of a base such as NaH to afford indole ester 17. Ester 17 is transformed to acid ID in a manner described above for Scheme 1.

Indoles substituted at the 2- and 3-position (IE) are prepared from 2- or 3-iodoindoles 19 via Pd-catalyzed Sonogashira coupling reactions (B. Hulin et al, J. Med. Chem., 1996, 39, 3897–3907) as shown in Scheme 5. Iodoindoles are obtained by procedures known in the literature (Bergman, J. and Venemalm, L. J., Org. Chem., 1992, 57(8), 2495–2497; Fiumana, A. and Jones, K., Chem. Commun., 1999, 17, 1761–2; Murugesan, N. et al, J. Med. Chem. 1998, 40(26), 5198–5218; Kelly, T. A. et al, J. Med. Chem., 1997, 40(15), 2430–2433; Merlic, C. A. et al, Tetrahedron Lett., 1997, 38(39), 6787–6790; Ketcha, D. M. et al, J. Org. Chem., 1989, 54(18), 4350–4356). The methyl ester 20 is transformed to aldehyde 21 as in Scheme 1 and subjected to reductive amination with glycine ester 5 to yield the secondary aminoester 22. Treatment with halide 7 (preferably a chloroformate), followed by reduction of the alkyne and saponification affords the 2- and 3-substitutted indoles IE.

Scheme 6 describes the synthesis of 3-substituted benzofurans and benzothiophenes IF. Compounds IF are prepared in a manner analogous to IE except that 3-bromobenzofurans and 3-bromobenzothiophenes 23 (Horgu, J. et al, Chem. Pharm. Bull., 1998, 46(1), 22–23; Cross, P. E. et al, J. Med. Chem., 1986, 29(9), 1643–1650) are used for the Pd mediated Sonogashira coupling reactions.

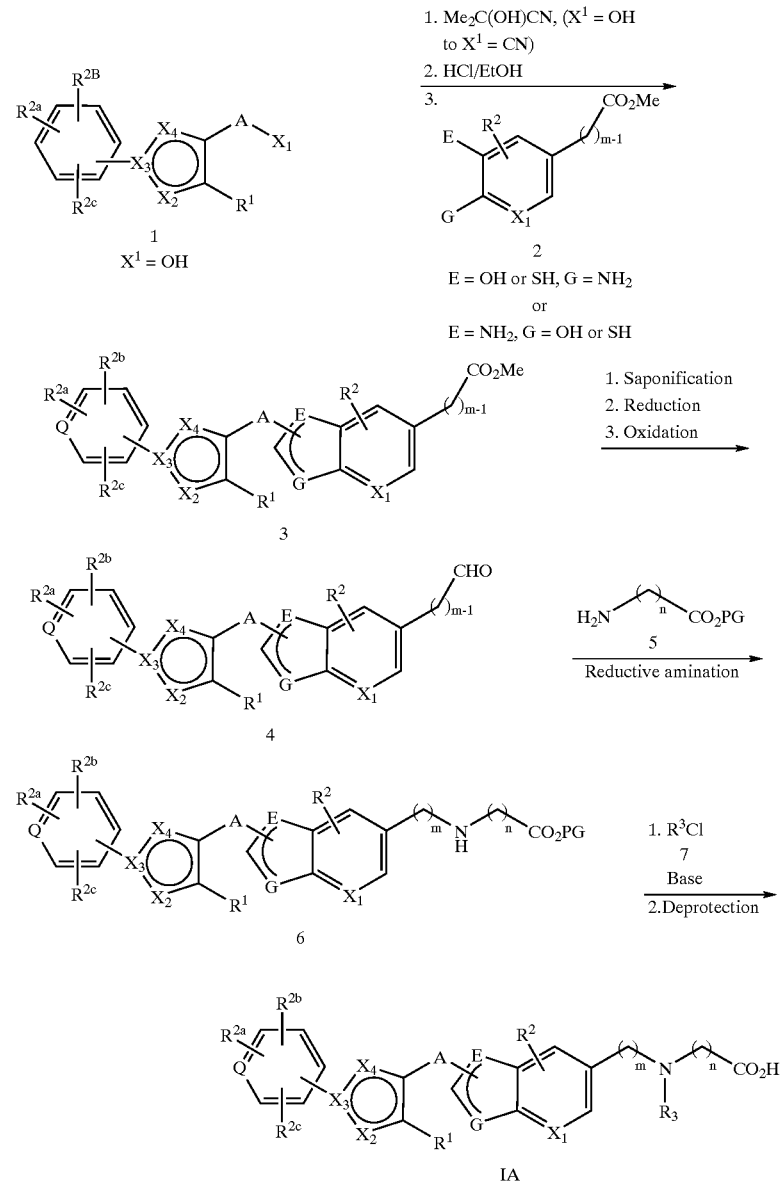

In Scheme 1, where E, M and G are each N, then A cannot be $CH_2$—O—.

Scheme 2

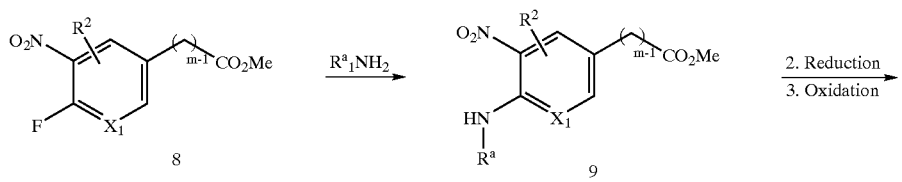

-continued
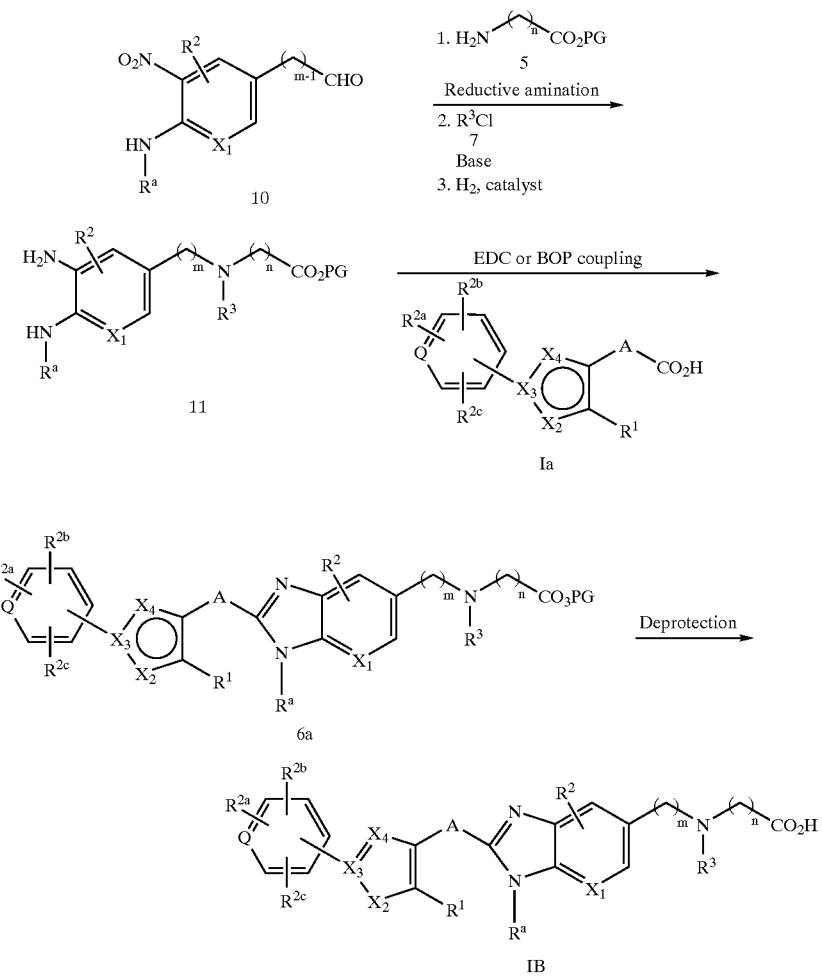
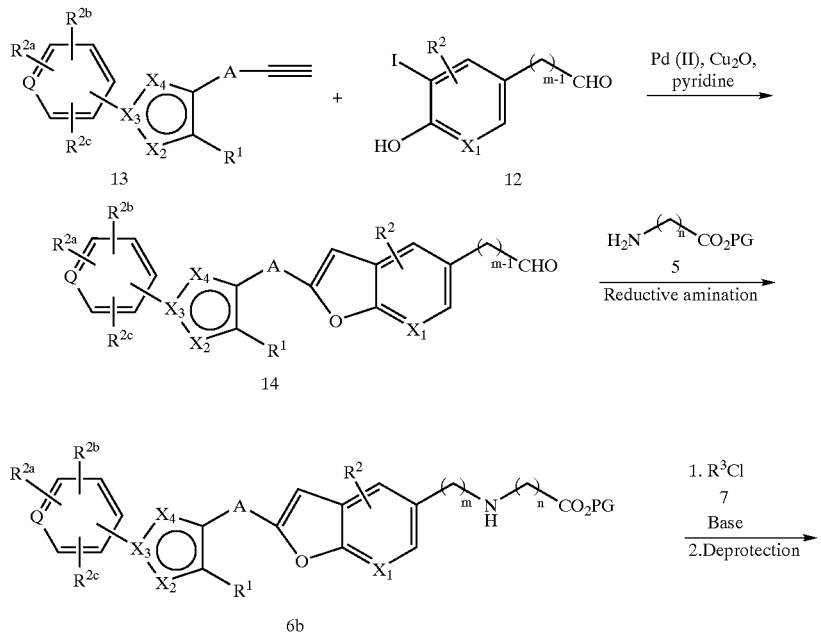
Scheme 3

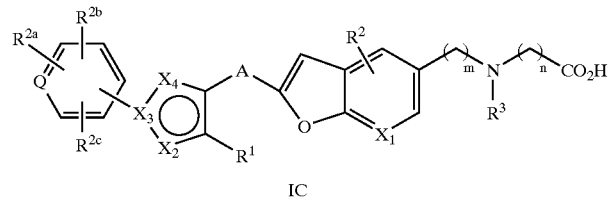
IC
Scheme 4
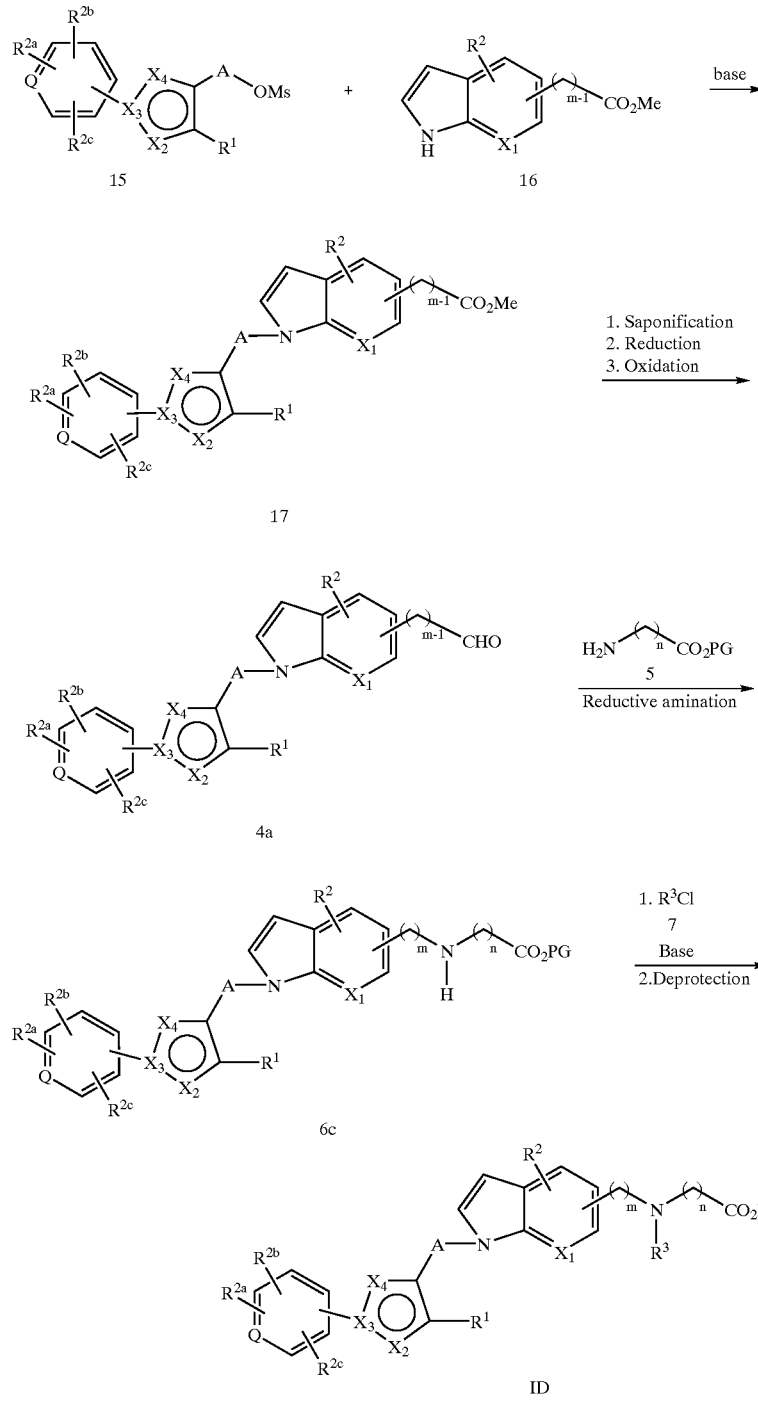

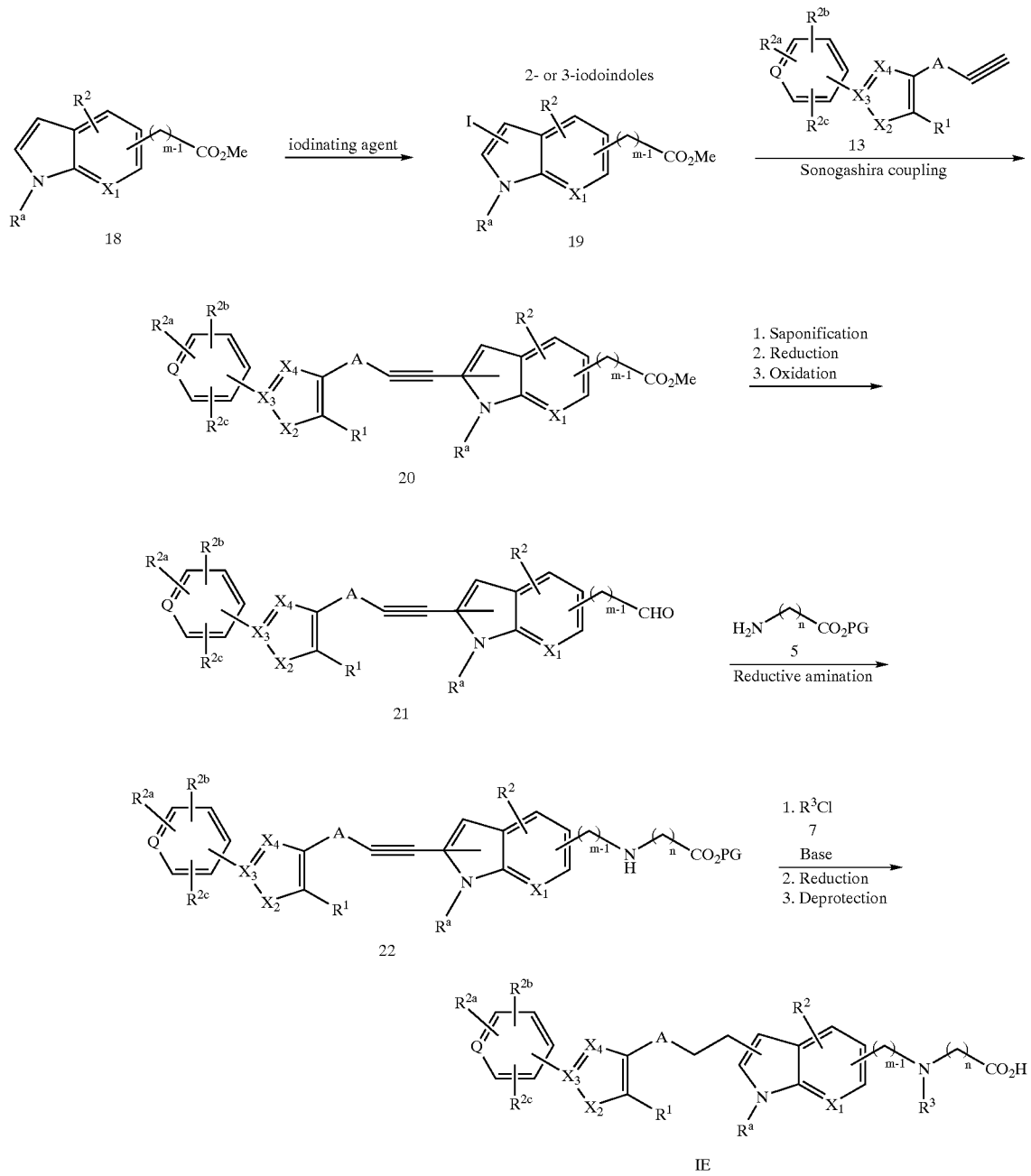
Scheme 5
2- and 3-substituted indoles
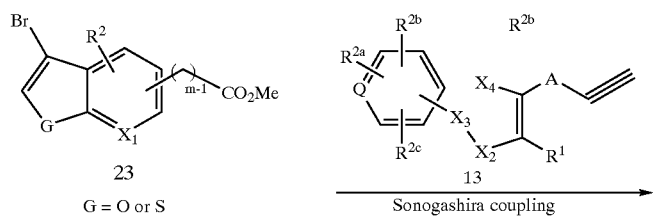
Scheme 6
3-substituted benzofurans/thiophenes -continued

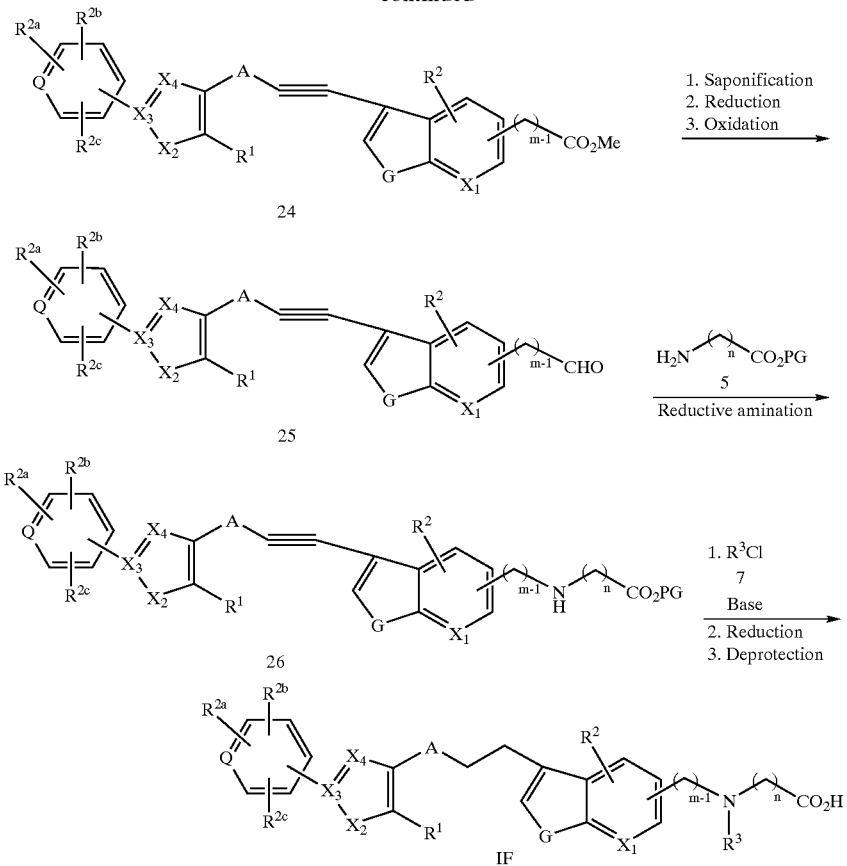

1. Saponification
2. Reduction
3. Oxidation

Reductive amination

1. R³Cl
   7
   Base
2. Reduction
3. Deprotection

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

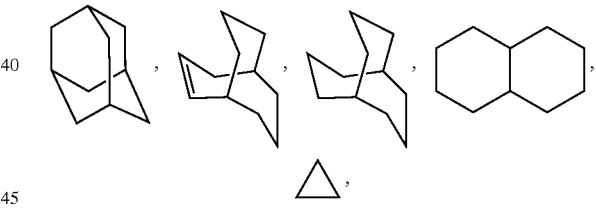

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

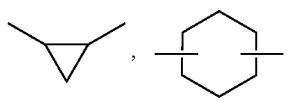

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH_2)_x^1$, $(CH_2)_x^2$, $(CH_2)_x^3$, $(CH_2)_p$, $(CH_2)_m$, or $(CH_2)_n$ includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$, $(CH_2)_x^1$, $(CH_2)_x^2$, $(CH_2)_x^3$ or $(CH_2)_m$ or $(CH_2)_n$ group to form a cycloalkyl group therewith.

Examples of $(CH_2)_x$, $(CH_2)_x^1$, $(CH_2)_x^2$, $(CH_2)_x^3$, $(CH_2)_p$, $(CH_2)_m$, $(CH_2)_n$, alkylene, alkenylene and alkynylene include

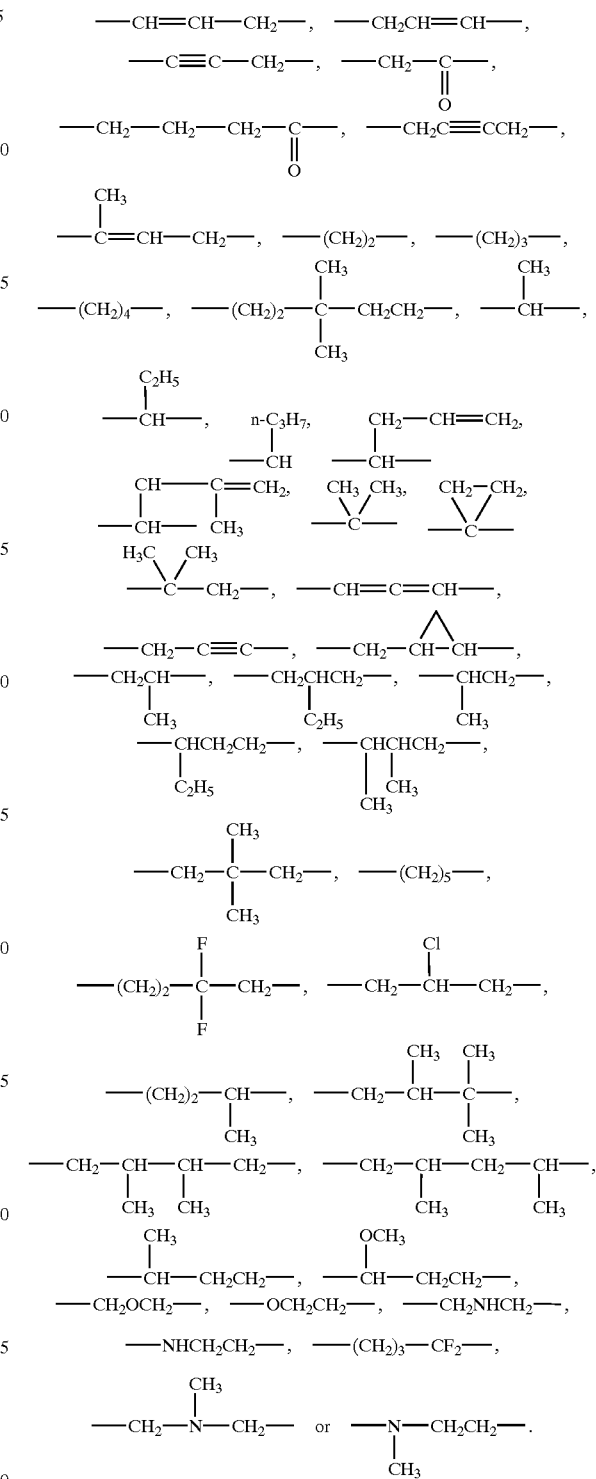

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

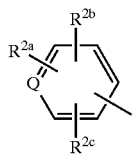

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

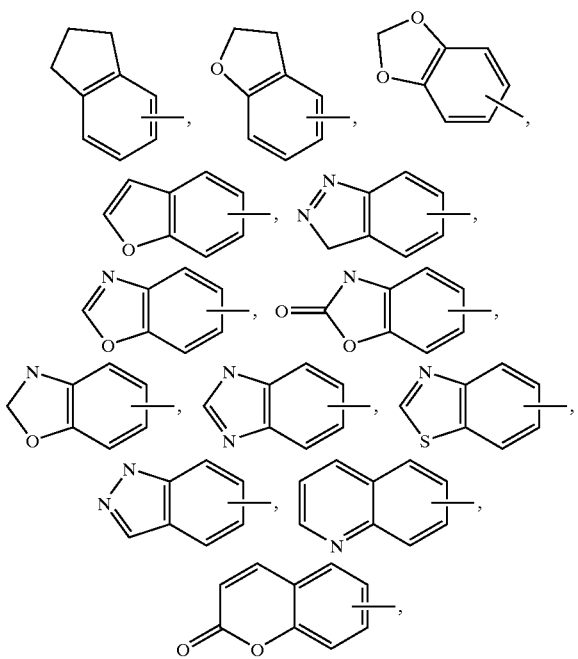

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

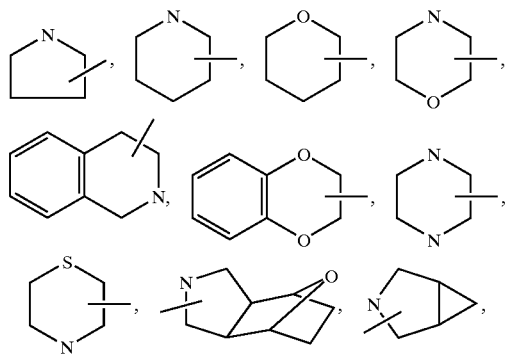

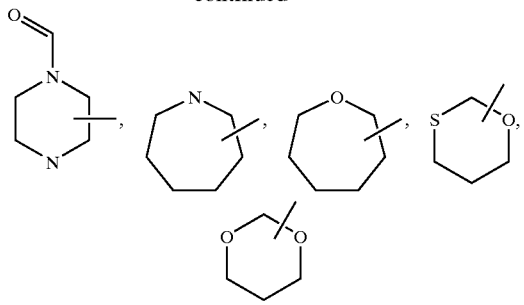

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

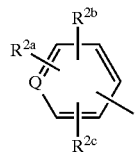

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the substituents for alkyl or aryl set out above. Examples of heteroaryl groups include the following:

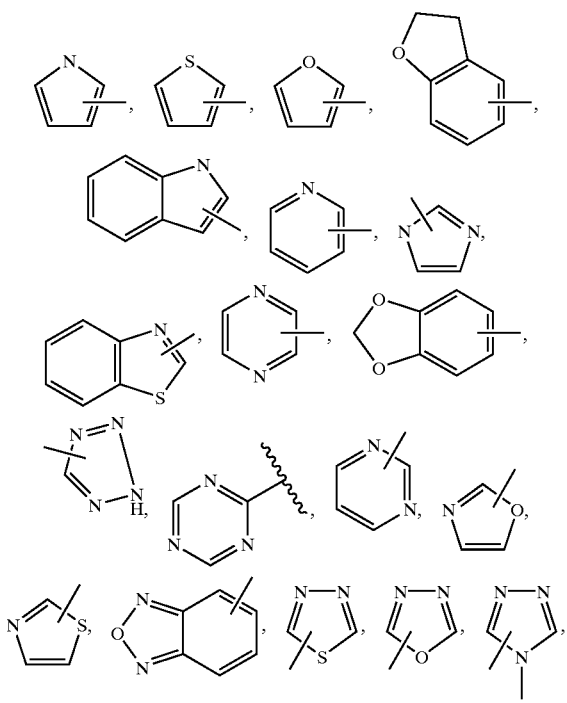

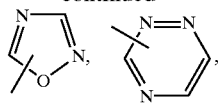

and the like.
Examples of

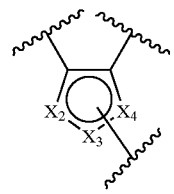

groups include, but are not limited to:

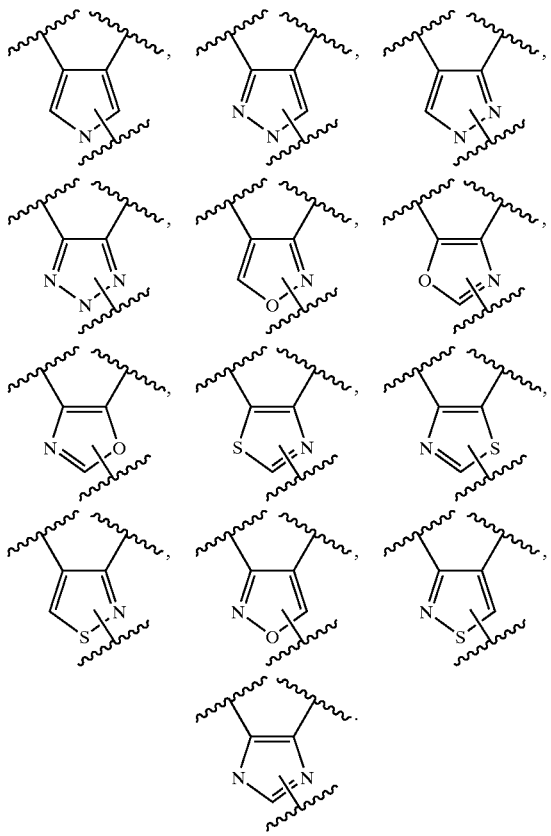

The term "cycloheteroalkylalkyl" as used herein alone or as part of another group refers to cycloheteroalkyl groups as defined above linked through a C atom or heteroatom to an alkylene or alkenylene as defined above.

The term "heteroarylalkyl" or "heteroarylalkenyl" as used herein alone or as part of another group refers to a heteroaryl group as defined above linked through a C atom or heteroatom to an alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups:

(1-alkanoyloxy)alkyl such as,

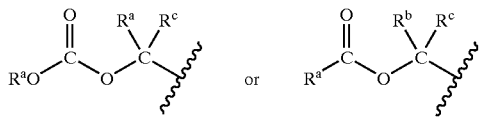

wherein $R^a$, $R^b$ and $R^c$ are H, alkyl, aryl or arylalkyl; however, $R^aO$ cannot be HO.

Examples of such prodrug esters $R^4$ include

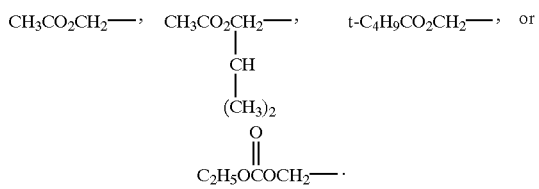

Other examples of suitable prodrug esters $R^4$ include

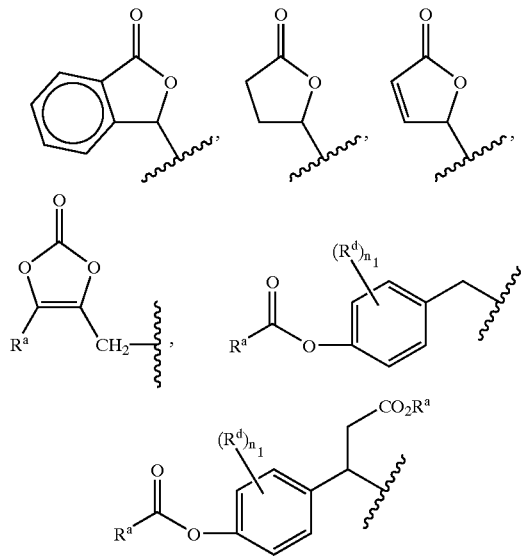

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents or lipid modulating agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent or lipid modulating agents which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

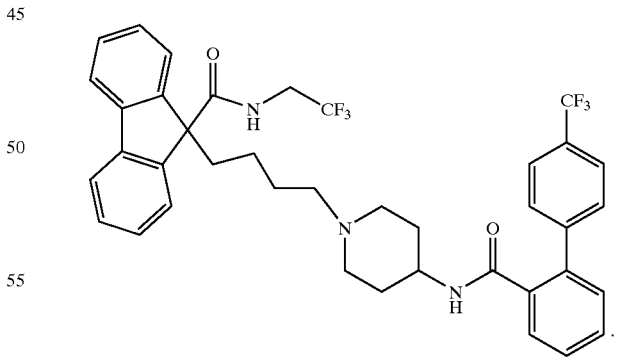

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, C1–1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal Na$^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. application Ser. No. 09/679,027, filed Oct. 4, 2000 (attorney file LA49 NP), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27 NP), employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application No. 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432, 971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5- tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. No. 5,362,727, U.S. Pat. No. 5,366,973, U.S. Pat. No. 5,225,401, U.S. Pat. No. 4,722,810, U.S. Pat. No. 5,223,516, U.S. Pat. No. 4,749,688, U.S. Pat. No. 5,552,397, U.S. Pat. No. 5,504,080, U.S. Pat. No. 5,612,359, U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)), CGS 30440 and MD100240 (Aventis).

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®. Dosages employed will be as set out in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following Examples represent preferred embodiments of the invention.

The following abbreviations are employed in the Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
Ac=acetyl
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LiAlH$_4$=lithium aluminum hydride
n-BuLi=n-butyllithium
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph3P=triphenylphosphine
Pd(OAc)$_2$=Palladium acetate
(Ph$_3$P)$_4$Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point The following Examples represent preferred embodiments of the invention.

EXAMPLE 1

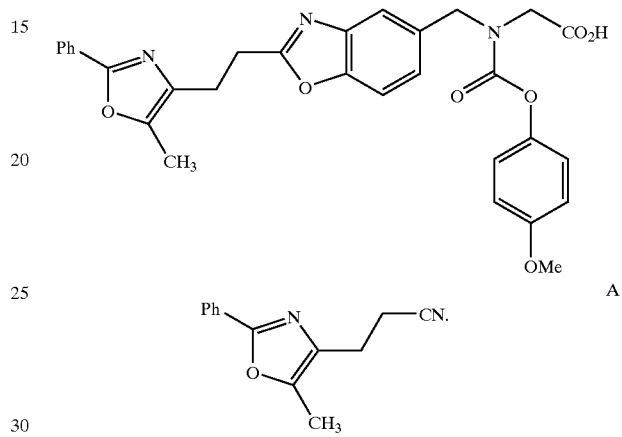

To a solution of 2-(5-methyl-2-phenyl-4-oxazolyl)ethanol (Maybridge, 10 gm, 49.3 mmol), acetone cyanohydrin (6.3 gm, 74 mmol), Ph$_3$P (12.9 gm, 49.2 mmol) in 25 ml THF at 0° C. was added DEAD (12.9 gm, 1.5 mmol) dropwise. The reaction mixture was allowed to warm to rt and stirred overnight. Evaporation followed by purification by flash chromatography (30% EtOAc:hexanes) yielded 2.69 gm pure product (Part A compound)+5.9 gm impure fractions (total yield: approx 75–80%).

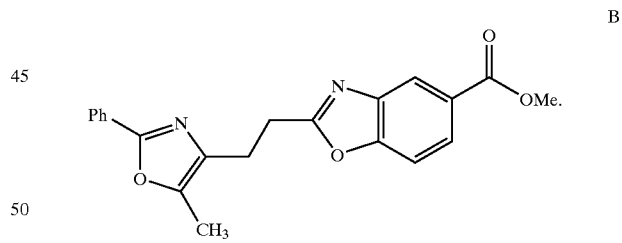

Reference: P. D. Edwards et al. J. Med. Chem. 1995, 38, 3972–3982.

A solution of anhydrous EtOH (1 ml) in CHCl$_3$ (2 ml) at 0° C. was treated with AcCl (1 ml) followed by Part A compound (178 mg, 0.84 mmol) in CHCl$_3$ (1 ml). The mixture was allowed to warm to rt and stirred for a total of 4 h. Solvents were evaporated to yield a pale yellow foam. The foam was dissolved in EtOH (3 ml) and to this solution was added 3-amino-4-hydroxybenzoic acid methyl ester hydrochloride (180 mg, 0.885 mmol) followed by Et$_3$N (200 μl, 1.44 mmol). The mixture was heated to 60° C. for 4 h, diluted with EtOAc, washed with 1N HCl, 1N NaOH, brine, dried (Na₂SO₄), evaporated, and purified by flash chromatography (30% to 40% EtOAc:hexanes) to yield a colorless, fluffy solid (Part B compound, 208 mg, 68%).

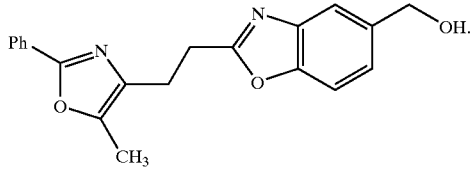
C

To Part B compound (100 mg, 0.276 mmol) in 3 ml THF was added a solution of LiOH.H₂O (30 mg, 0.71 mmol) in 1 ml H₂O dropwise and mixture stirred overnight. The mixture was acidified with 1N HCl, extracted into EtOAc, the combined organic layer washed with brine, dried (Na₂SO₄), and evaporated to yield ~100 mg of the, crude acid which was used as such for reduction.

Benzoxazole carboxylic acid obtained above (45 mg, 0.13 mmol) was dissolved in 4 ml THF. To this was added N-methylmorpholine (30 μl, 0.3 mmol) followed by isobutylchloroformate (20 μl, 0.15 mmol) dropwise. The mixture became turbid within minutes. The mixture was allowed to stir for 2 h, filtered through a cotton plug and rinsed with THF. To the filtrate was added solid NaBH₄ (20 mg, 0.53 mmol) followed by MeOH (dropwise, 0.5 ml). Vigorous effervescence ensued following NaBH₄ addition. The mixture was stirred for 2 h, quenched with 1N HCl, extracted into EtOAc (x2), the combined organic layer washed with brine, dried (Na₂SO₄), evaporated to yield a residue which was purified by PrepHPLC (YMC S5 ODS 20×250 mm; 10 min gradient; 40% B to 100% B) to obtain 10 mg of Part C compound (23%).

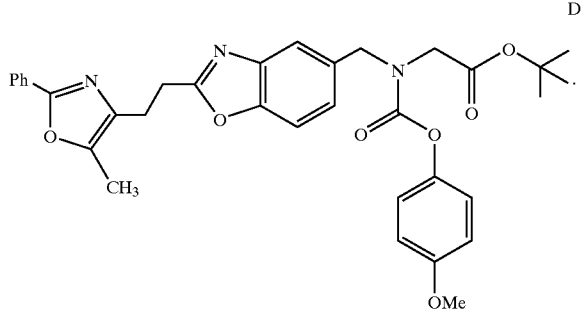
D

To a suspension of Dess-Martin periodinane (30 mg, 0.07 mmol) in CH₂Cl₂ (4 ml) was added a solution of Part C compound (10 mg, 0.03 mmol) in CH₂Cl₂ (1 ml) dropwise. The reaction mixture turned yellow and was allowed to stir for 2 h. The reaction mixture was evaporated and partially purified through a 2 gm silica gel cartridge to yield 10 mg of enriched aldehyde which was used as such for reductive amination.

To the partially purified aldehyde, glycine t-butyl ester hydrochloride, and CH₂Cl₂ (3 ml) was added Et₃N followed by NaBH(OAc)₃ and the mixture was stirred overnight. A second portion of NaBH(OAc)₃ was added to drive the reaction to completion. The reaction mixture was taken up in EtOAc, washed with sat aq. NaHCO₃, brine, dried (Na₂SO₄), and evaporated to yield 15 mg of crude product mixture (Part D1 compound) which was used as such for carbamate synthesis.

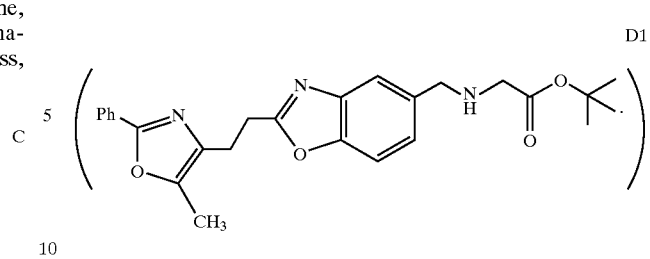
D1

To above secondary amine (Part D1 compound) dissolved in CH₂Cl₂ (2 ml) was added sequentially pyridine (20 μl, 0.248 mmol) and a solution of 4-methoxyphenyl-chloroformate (20 mg, 0.107 mmol) in 0.2 ml CH₂Cl₂. The reaction mixture was allowed to stir for 15 min, diluted with CH₂Cl₂, washed with 1N HCl, brine, dried (Na₂SO₄), evaporated to yield a residue which was purified by PrepH-PLC (YMC S5 ODS 20×250 mm; 10 min gradient; 70% B to 100% B) to yield 5 mg (28% for 3 steps) of Part D compound.

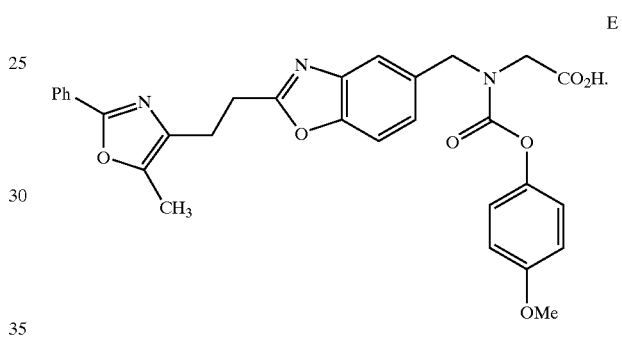
E

To a solution of Part D compound (5.0 mg, 0.0084 mmol) in CH₂Cl₂ (1.5 ml) at room temperature was added TFA (0.5 ml) dropwise. The reaction was stirred for 3 h and concentrated. The residue was purified by PrepHPLC (YMC S5 ODS 20×100 mm; 20 mL/min; 10 min continuous gradient from 30% B:70% A to 100% B where solvent A=90:10:0.1H₂O:MeOH:TFA and solvent B=90:10:0.1 MeOH:H₂O:TFA) to yield 1 mg of title compound. [M+H⁺]=542.33.

¹H NMR (400 MHz, CDCl₃) δ 2.303 (s, 3H), 3.1–3.2 (br t, 2H), 3.3–3.4 (br t, 2H), 3.7720 (s, 3H), 4.0661 (d, J=8.4 Hz, 2H), 4.786 (d, J$_{AB}$=41 Hz, 2H), 6.854 (dd, J=8.8, 5.3 Hz, 2H), 7.039 (dd, J=11.4, 8.8 Hz, 2H), 7.3202 (t, J=9.2 Hz, 1H), 7.4–7.52 (m, 4H), 7.6555 (d, J=8.8 Hz, 1H), 7.9–8.0 (m, 2H)

EXAMPLE 2

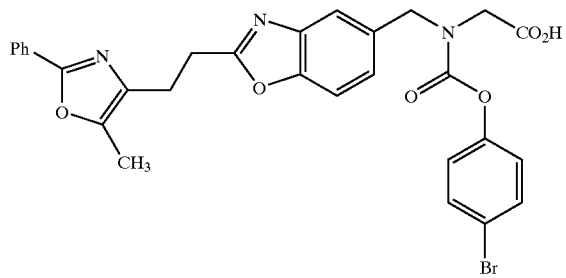

-continued

A

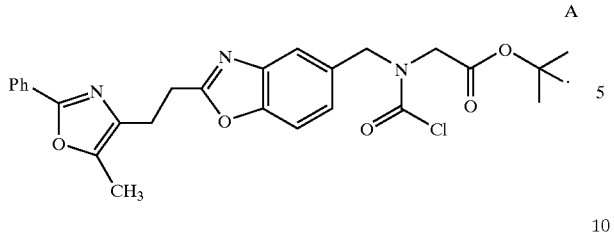

To a solution of Part D1 compound (260 mg, 0.58 mmol) and Et₃N (0.16 mL, 1.16 mmol, 2 equiv) in CH₂Cl₂ (20 mL) at r.t. was added a solution of phosgene (1.93M in toluene, 0.6 mL, 1.16 mmol, 2 equiv) and the mixture allowed to stir for 3 h. The mixture was washed with H₂O, organic layer dried (Na₂SO₄), evaporated and the residue purified by flash chromatography (100% CH₂Cl₂) to yield 70 mg (24%) of Part A compound.

B

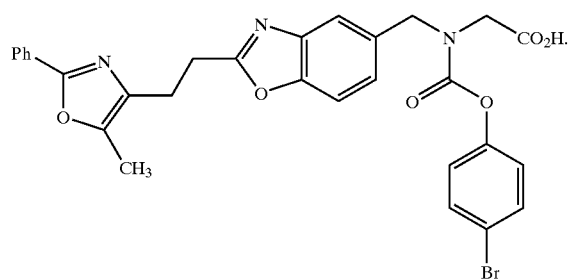

4-Bromophenol (2.2 mg, 0.013 mmol, 1.1 equiv) was dissolved in 0.1 mL anhydrous DMF. KOt-Bu (3.9 mg, 0.036, 3 equiv) was then added and the reaction mixture was stirred for 15 min. A solution of Part A compound (6 mg, 0.012 mmol, 1 equiv) in 0.1 mL DMF was then added. After 5 min, the mixture was evaporated, resuspended in 1 mL CH₂Cl₂ and purified by flash chromatography (30% EtOAc:hexanes). The purified ester was dissolved in 0.2 mL CH₂Cl₂ and treated with 0.02 mL TFA and the mixture was allowed to stir for 16 h. Evaporation followed by purification by preparative HPLC (YMC S5 ODS 20×100 mm; 10 min continuous gradient from 30% B:70% A to 100% B where solvent A=90:10:0.1 H₂O:MeOH:TFA and solvent B=90:10:0.1 MeOH:H₂O:TFA) to afford 1.1 mg (16%) of title compound. [M+H⁺]=590.09/592.15

EXAMPLE 3

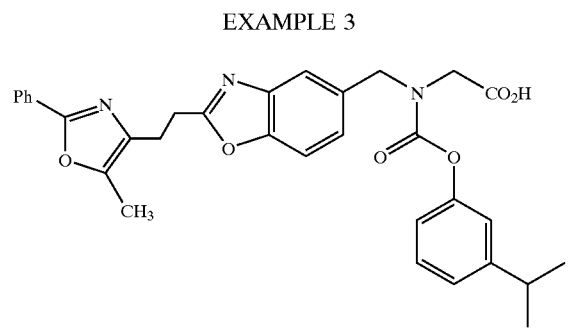

The tile compound was prepared in an analogous manner to that of Examples 1 and 2. [M+H⁺]=554.24

EXAMPLE 4

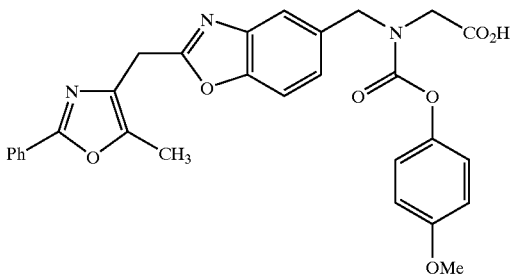

A

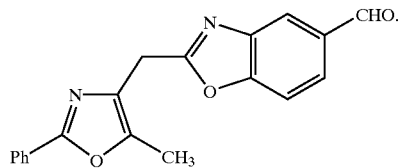

NaCN (442 mg, 9 mmol, 1.1 equiv) was dispersed in 6 mL DMSO and heated at 140° C. for 30 min. To this solution was added (5-methyl-2-phenyl-4-oxazolyl)methyl chloride (1.7 gm, 8.2 mmol, prepared according to Malamas, Michael S. et al. *J. Med. Chem.* 39 (1); 1996; 237–245) in 5 mL DMSO and the reaction mixture was stirred at 120° C. for 15 min. The mixture was poured into water, extracted with EtOAc (20 mL×3), and the combined organic layer washed with brine (20 mL×3), and evaporated to provide a residue which was purified by flash chromatography (30% EtOAc:hexanes) to afford 600 mg (37%) of Part A compound as a yellow solid.

B

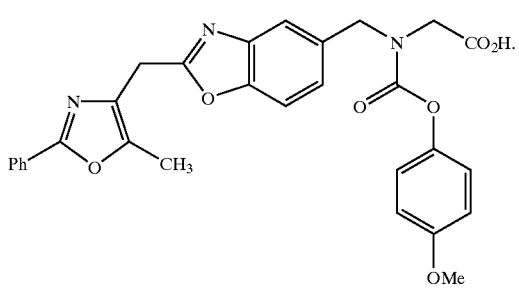

Part B compound was prepared from Part A compound in a manner analogous to the sequence describing the synthesis of Example 1 Part D compound.

C

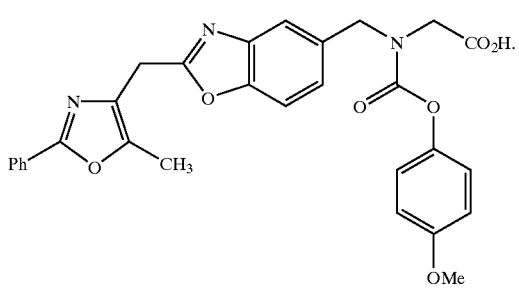

Part B compound (6 mg, 0.0189 mmol), glycine methyl ester hydrochloride (3.6 mg, 0.028 mmol, 1.5 equiv), and NaBH(OAc)₃ were stirred together in 0.2 mL CH₂Cl₂ at r.t. for 16 h after which the mixture was evaporated and the residue purified by preparative HPLC conditions (YMC ODS 20×100 mm flow rate=20 mL/min; 10 min continuous gradient from 70% B:30% A to 100% B where solvent A=90:10:01 H₂O:MeOH:TFA and solvent B=90:10:0.1 MeOH:H₂O:TFA) to give 3 mg (40%) of the desired secondary amine.

To a solution of the secondary amine above (3 mg, 0.0077 mmol) and Et$_3$N (3 mg, 0.03 mmol, 4 equiv) in 1 mL CH$_2$Cl$_2$ was added 4-methoxyphenylchloroformate (3 mg, 0.015 mmol, 2 equiv) and the mixture stirred for 5 min. The reaction mixture was evaporated to dryness and used as such for hydrolysis.

The crude methyl ester (from above) and LiOH.H$_2$O (2 mg, 0.047 mmol, 6 equiv) were stirred together in 10:1 MeOH:H$_2$O (0.5 mL) for 16 h. The mixture was acidified with 1N HCl and extracted into 1 mL EtOAc. Organic layer was evaporated and residue was purified by preparative HPLC conditions (YMC ODS 20×100 mm flow rate=20 mL/min; 10 min continuous gradient from 70% B:30% A to 100% B where solvent A=90:10:01 H$_2$O:MeOH:TFA and solvent B=90:10:0.1 MeOH:H$_2$O:TFA). The desired fractions were neutralized with K$_2$CO$_3$, evaporated, and the pH of the residual solution adjusted to 7, and then extracted into EtOAc (2 mL) to yield 1.3 mg (32% overall) of title compound as a gum. [M+H$^+$]=528.18

EXAMPLE 5

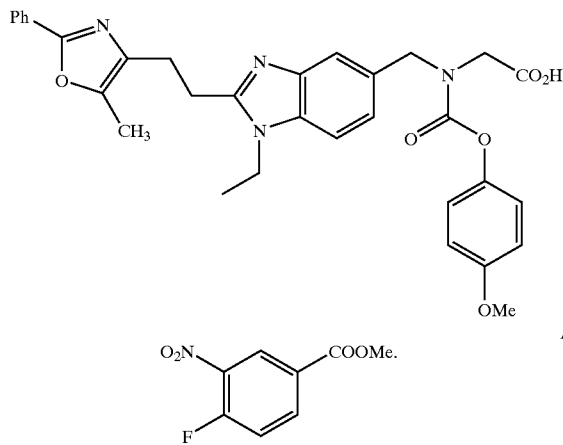

A

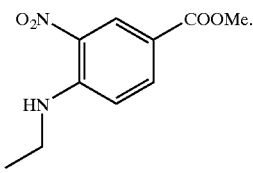

B

4-Fluoro-3-nitrobenzoic acid (1.37 gm, 7.41 mmol) was dissolved in a methanolic solution of HCl and heated to 50° C. for 16 h. Evaporation of the resulting mixture yielded 1.45 gm (7.29 mmol, 98%) of compound A as a colorless solid.

A solution of 2M ethylamine in THF (1.2 mL, 2.4 mmol, 1.5 equiv.) was added to a solution of 4-fluoro-3-nitrobenzoic acid methyl ester (317 mg, 1.59 mmol) in 10 mL THF and the mixture was allowed to stir overnight. Evaporation followed by purification by flash chromatography (ISCO CombiFlash™, 10 gm silica; 0% to 100% EtOAc-hexanes) yielded 322 mg (93%) of compound B as a yellow solid.

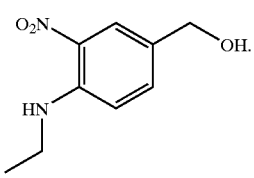

C

To a solution of compound B (125 mg, 0.56 mmol) in THF (6 ml) at r.t. was added a 2M solution of LiBH$_4$ (1.35 mL, 2.7 mmol, 4.8 equiv.) and the resulting mixture stirred overnight. The reaction was quenched with 1N HCl and extracted thoroughly into EtOAc (10 mL×3). The combined organic layer was washed with brine, dried (Na$_2$SO$_4$), and evaporated to yield an orange residue which was purified by flash chromatography (ISCO CombiFlash™, 10 gm silica; 0% to 100% EtOAc-hexanes) to afford a yellow solid (compound C) weighing 67 mg (60%).

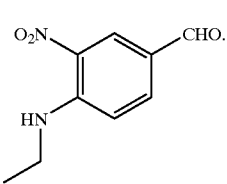

D

To a suspension of the Dess-Martin sulfurane reagent (1.7 gm, 4 mmol, 1.5 equiv.) in CH$_2$Cl$_2$ (30 mL) was added a solution of 4-ethylamino-3-nitrobenzyl alcohol (compound C, 526 mg, 2.68 mmol, 1 equiv.) in 20 mL CH$_2$Cl$_2$ and the resulting mixture was stirred for 16 h. The reaction mixture was diluted with 50 mL ether and treated with 50 mL of 1:1 aqueous solution of NaHCO$_3$:sodium thiosulfate for 1 h. The resulting clear solution was extracted thoroughly with EtOAc (50 mL×3) and the combined organic layer was washed with brine, dried (Na$_2$SO$_4$), and evaporated to yield a residue which was chromatographed (ISCO CombiFlash™, 35 gm silica; 0% to 100% EtOAc-hexanes) to yield 348 mg (67%) of compound D as a yellow solid.

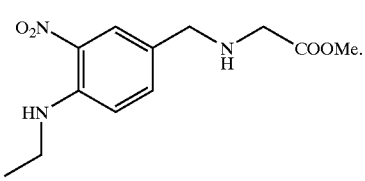

E

4-Ethylamino-3-nitrobenzaldehyde (compound D) (348 mg, 1.79 mmol), glycine methyl ester hydrochloride (675 mg, 5.38 mmol, 3 equiv.), sodium triacetoxyborohydride (1.76 gm, 8.34 mmol, 4.6 equiv.), Et$_3$N (1.5 mL, 10.8 mmol, 6 equiv.), and 1,2-dichloroethane (50 mL) were stirred together at 55° C. for 2 h. The reaction mixture was partitioned between CH$_2$Cl$_2$ and saturated aqueous NaHCO$_3$ and the aq. layer extracted with CH$_2$Cl$_2$ (50 mL×2). The combined organic layer was washed with brine, dried (Na$_2$SO$_4$), evaporated and purified by flash chromatography (ISCO CombiFlash™, 35 gm silica; 0% to 100% EtOAc-hexanes) to yield 417 mg (87%) of compound E as a red oil.

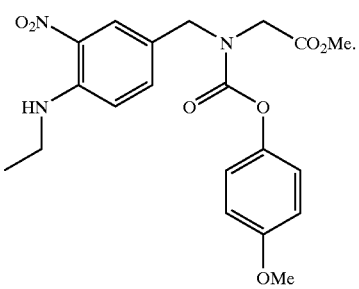

F

To compound E (208 mg, 0.78 mmol) in $CH_2Cl_2$ was added pyridine (100 μL, 1.24 mmol, 1.6 equiv.) followed by 4-methoxyphenylchloroformate (140 μL, 0.94 mmol, 1.2 equiv.) and the mixture was stirred for 1 h. Evaporation and purification by flash chromatography (ISCO CombiFlash™, 10 gm silica; 0% to 100% EtOAc-hexanes) afforded 263 mg (81%) of compound F as a yellow oil (solidified to a yellow solid in the freezer).

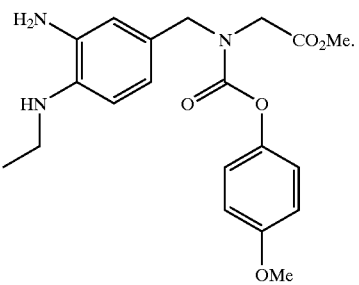

G

Compound F (66 mg, 0.158 mg) was hydrogenated in the presence 10% Pd—C (30 mg) and MeOH (10 mL) for 2 h at atmospheric pressure and r.t. The reaction mixture was filtered and evaporated to yield 47 mg (77%) of compound G as a colorless oil.

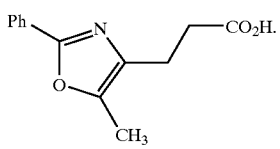

H

To 3-(2-methyl-5-phenyl-oxazol-4-yl)propanol (133 mg, 0.613 mmol) in acetone (2 mL) was added Jones reagent via a Pasteur pipette (~15 drops) and the resulting mixture stirred for 7 h at rt. Evaporation followed by purification by preparative HPLC (YMC S5 ODS reverse phase column; 20×100 mm; flow rate=20 mL/min; 10 min continuous gradient from 30% B:70% A to 100% B where solvent A=90:10:0.1 $H_2O$:MeOH:TFA and solvent B=90:10:0.1 MeOH:$H_2O$:TFA) yielded 91 mg (64%) of a colorless oil (compound H).

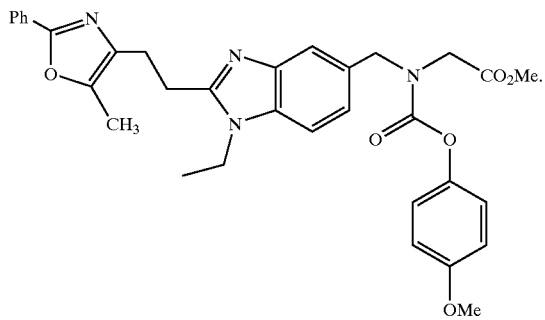

I

To a mixture of 3-(2-methyl-5-phenyl-oxazol-4-yl) propanoic acid (compound H), compound G, and HOAt in $CH_2Cl_2$ was added diisopropylcarbodiimide dropwise. After 3 h, all amine was consumed and several products (>13) were seen by HPLC. The reaction mixture was evaporated to dryness and purified by preparative HPLC (YMC S5 ODS reverse phase column; 20×100 mm; flow rate=20 mL/min; 10 min continuous gradient from 30% B:70% A to 100% B where solvent A=90:10:0.1 $H_2O$:MeOH:TFA and solvent B=90:10:0.1 MeOH:$H_2O$:TFA) to afford 10 mg (14%) of compound I as a colorless oil. Side products included the corresponding monoamides from the primary and secondary amines, DIC adducts and the DIC adduct of a monoamide. $[M+H^+]=583.10$.

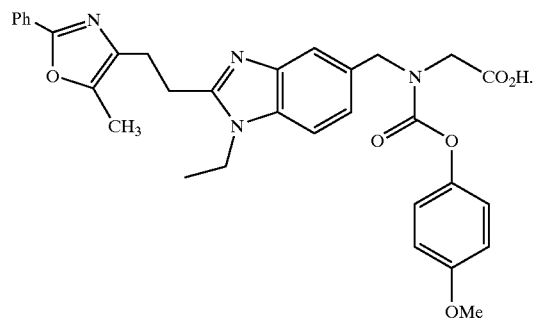

J

To a solution of compound I (10.0 mg, 0.017 mmol) in THF-$H_2O$ (4:1, 2.5 mL) at room temperature was added LiOH.$H_2O$ (11 mg, 0.262 mmol, 15 equiv.) all at once. The reaction mixture was stirred at room temperature for 3 h, acidified to pH ~4, and extracted into EtOAc (10 mL×2). The combined organic layer was washed with brine, dried ($Na_2SO_4$) and evaporated to yield a colorless oil which was purified by preparative HPLC (YMC S5 ODS reverse phase column; 20×100 mm; flow rate=20 mL/min; 10 min continuous gradient from 30% B:70% A to 100% B where solvent A=90:10:0.1 $H_2O$:MeOH:TFA and solvent B=90:10:0.1 MeOH:$H_2O$:TFA) 3.4 mg (35%) of title compound as a colorless oil. $[M+H^+]=569.17$.

EXAMPLE 6

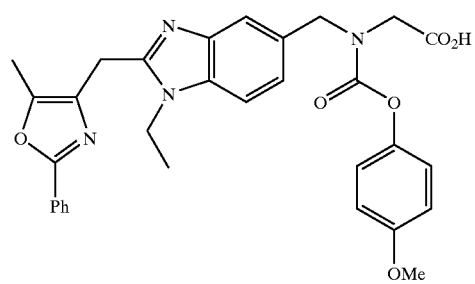

A

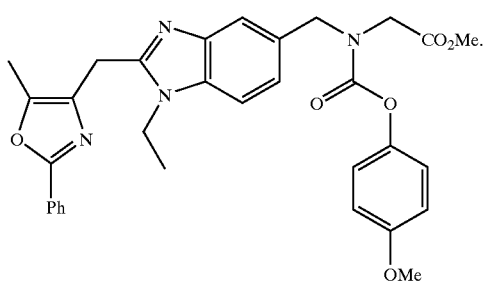

To a mixture of 3-(2-methyl-5-phenyl-oxazol-4-yl)acetic acid (Maybridge, 39 mg, 0.18 mmol, 1.16 equiv.) and Example 5 compound G (60 mg, 0.155 mmol) in CH$_3$CN (7 mL) was added benzotriazol-1-yloxy-tris(dimethylamino)-phosphonium hexafluorophosphate (125 mg, 0.28 mmol, 1.82 equiv.) and the resulting mixture stirred for 16 h. The reaction mixture was evaporated to dryness and purified by preparative HPLC (YMC S5 ODS reverse phase column; 20×100 mm; flow rate=20 mL/min; 10 min continuous gradient from 30% B:70% A to 100% B where solvent A=90:10:0.1 H$_2$O:MeOH:TFA and solvent B=90:10:0.1 MeOH:H$_2$O:TFA) followed by flash chromatography (ISCO CombiFlash™, 10 gm silica; 0% to 20% MeOH—CH$_2$Cl$_2$) to afford 4 mg (5%) of compound A as a brown oil. [M+H$^+$]569.11.

B

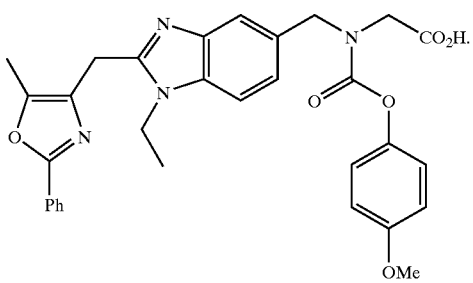

To a solution of compound A (4.0 mg, 0.007 mmol) in THF-H$_2$O (4:1, 1.2 mL) at room temperature was added LiOH.H$_2$O (6 mg, 0.14 mmol, 20 equiv.) all at once. The reaction mixture was stirred at room temperature for 1 h, acidified to pH ~2, and extracted into EtOAc (10 mL×2). The combined organic layer was washed with brine, dried (Na$_2$SO$_4$) and evaporated to yield a colorless oil which was purified by preparative HPLC (YMC S5 ODS reverse phase column; 20×100 mm; flow rate=20 mL/min; 10 min continuous gradient from 30% B:70% A to 100% B where solvent A=90:10:0.1 H$_2$O:MeOH:TFA and solvent B=90:10:0.1 MeOH:H$_2$O:TFA) to afford 1.7 mg (44%) of title compound as a yellow oil. [M+H$^+$]=555.09.

$^1$H NMR (400 MHz, CDCl$_3$) δ 1.5879 (t, J=6.6 Hz, 3H), 2.4914 (s, 3H), 3.7467 (br s, 5H), 4.4992 (d, J=10.12 Hz, 2H), 4.69–4.72 (m, 3H), 4.8426 (s, 1H), 6.8240 (dd, J=8.8, 6.6 Hz, 2H), 6.98–7.04 (m, 2H), 7.37–7.42 (m, 3H), 7.48–7.6 (m, 2H), 7.86–7.85 (m, 3H).

EXAMPLE 7

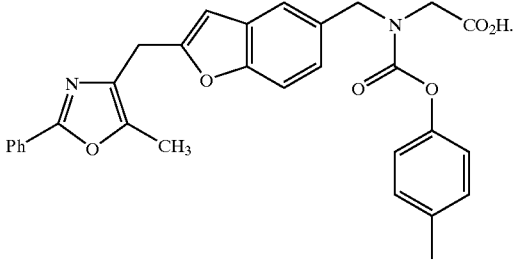

A

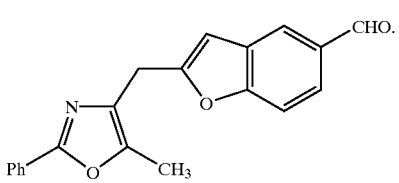

Reference: B. Hulin et al. *J. Med. Chem.* 1996, 39, 3897–3907.

To a slurry of cuprous oxide (55 mg, 0.385 mmol, 0.67 equiv) in 1 mL pyridine was added a solution of the compound A1 (prepared as described in B. Hulin et al. *J. Med. Chem.* 1996, 39, 3897–3907, 113 mg, 0.577 mmol, 1 equiv) in 1 mL pyridine followed by a solution of 3-iodo-4-hydroxybenzaldehyde (138 mg, 0.585 mmol, 1 equiv) in 0.5 mL pyridine.

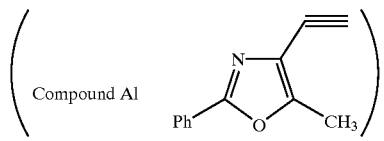

Bis(triphenylphosphine)palladium (II) chloride (9 mg, 0.02 equiv) was added as a solid and the mixture was heated to reflux for 3 h. The reaction mixture was evaporated in vacuo, taken up in EtOAc (20 mL), washed with 1N HCl (10 mL×2), brine, dried (Na$_2$SO$_4$), filtered, and evaporated under reduced pressure to yield a dark residue which was purified by flash chromatography (20% EtOAc-hexanes) to afford 76 mg (42%) of compound A as a yellow solid.

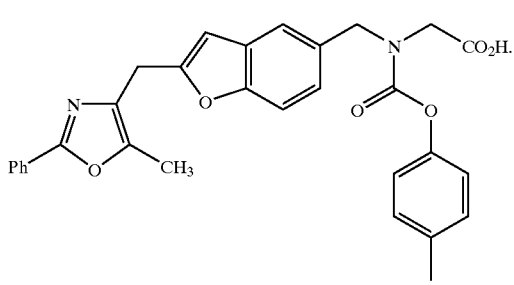

B

To a mixture of compound A (65 mg, 0.205 mmol), glycine methyl ester hydrochloride (83 mg, 0.66 mmol, 3.2 equiv) and dichloroethane (10 mL) was added Et$_3$N (150 μL, 0.75, 3.7 equiv) followed by NaBH(OAc)$_3$ (90 mg, 0.427 mmol, 2 equiv) and the resulting mixture allowed to stir for 12 h at rt. A second portion of NaBH(OAc)$_3$ (90 mg, 0.427 mmol, 2 equiv) was added at this point and the mixture stirred for a further 12 h. The mixture was diluted with CH$_2$Cl$_2$ (20 mL), washed with sat. aq. NaHCO$_3$, brine, dried (Na$_2$SO$_4$), and evaporated to yield 84 mg of the crude secondary amine which was used as such for the next reaction.

To a solution of secondary amine above (21.0 mg, 0.054 mmol) in CH$_2$Cl$_2$ (3 mL) at room temperature was added pyridine (13 μL, 0.161 mmol, 3 equiv.) followed by 4-methylphenylchloroformate (13 μL, 0.0905 mmol, 1.7 equiv) and the mixture stirred for 3.5 h. The reaction mixture was washed with 1N HCl (1 mL), brine (1 mL), dried (Na$_2$SO$_4$), and evaporated in vacuo to yield a yellow oil which was used as such for hydrolysis. [M+H$^+$]=525.07.

The crude ester above was dissolved in 4:1 THF:H$_2$O (5 mL) and LiOH.H$_2$O (10 mg, 0.24 mmol, 4.4 equiv) added all at once. After stirring at r.t. for 2 h, the mixture was acidified with 1N HCl and extracted into EtOAc (5 mL×3). The combined organic layer was washed with brine, dried (Na$_2$SO$_4$), and evaporated to yield a residue which was purified by preparative HPLC (YMC S5 ODS reverse phase column; 30×75 mm; flow rate=20 mL/min; 10 min continuous gradient from 70% B:30% A to 100% B where solvent A=90:10:0.1 H$_2$O:MeOH:TFA and solvent B=90:10:0.1 MeOH:H$_2$O:TFA) to afford 22.7 mg (82%) of the desired product as a yellow oil. [M+H$^+$]=511.07.

$^1$H NMR (400 MHz, CDCl$_3$) δ 2.2270 (s, 3H), 2.3094 (s, 3H), 3.9253 (d, J=23.7 Hz, 2H), 3.9692 (s, 2H), 4.62222 (d, J$_{AB}$=51 Hz, 2H), 6.4540 (d, J=5.72 Hz, 1H), 6.8909 (dd, J=8.4, 4.0 Hz, 2H), 7.05–7.2 (m, 3H), 7.26–7.44 (m, 5H), 7.85–7.9 (m, 2H).

EXAMPLE 8

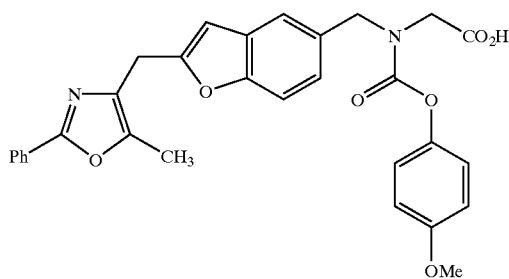

The title compound was prepared in a manner analogous to Example 7. [M+H$^+$]=527.05.

EXAMPLE 9

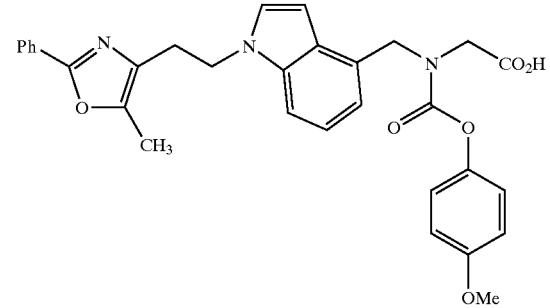

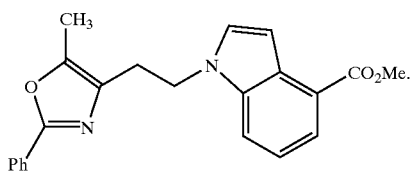

A

To a mixture of indole-4-carboxylic acid methyl ester (100 mg, 0.57 mmol), sodium hydride (60% dispersion, 30 mg, 0.855 mmol) in 5 mL anhydrous DMF was added 2-(5-methyl-2-phenyloxazol-4-yl)ethanol methanesulfonate (170 mg, 0.57 mmol) in 5 mL anhydrous DMF dropwise, and the mixture was then heated to reflux for 3 h. The reaction mixture was partitioned between H$_2$O (100 mL) and CH$_2$Cl$_2$ (100 mL). The aqueous phase was extracted with CH$_2$Cl$_2$ (2×50 mL). The combined organic extracts were washed with brine, dried (Na$_2$SO$_4$) and concentrated in vacuo. The residue was chromatographed (SiO$_2$; 70:30 Hex:EtOAc) to obtain compound A (220 mg, 99%) as yellow solid.

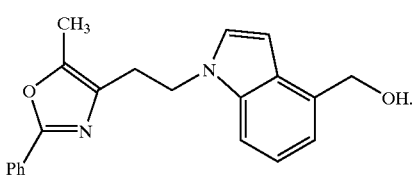

B

Compound A from above was dissolved in anhydrous THF (3 ml) under Ar. LAH (1.0 M in THF, 1.39 mL, 1.39 mmol) was added and the reaction mixture was heated under reflux overnight. The reaction mixture was partitioned between H$_2$O (100 mL) and EtOAc (100 mL). The aqueous phase was extracted with EtOAc (2×50 mL). The combined organic extracts were washed with brine, dried (Na$_2$SO$_4$) and concentrated in vacuo. The residue was chromato graphed (SiO$_2$, 100% EtOAc) to obtain compound B (200 mg, 99%) as yellow solid.

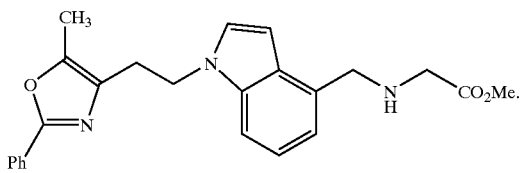

To a mixture of silica (SiO$_2$, 100 mg) and PCC (136 mg, 0.63 mmol) in 1 mL CH$_2$Cl$_2$, was added compound B (200 mg, 0.63 mmol) in 0.5 mL CH$_2$Cl$_2$, and the reaction was stirred at rt for 15 min. The reaction mixture was then poured onto a column (SiO$_2$, 50:50 EtOAc:Hex) to obtain the desired aldehyde as a yellow solid (110 mg, 50%).

The obtained aldehyde (110 mg, 0.63 mmol) was then dissolved in 1 mL CH$_2$Cl$_2$ and to this solution was added sodium triacetoxyborohydride (135 mg, 0.318 mmol) and glycine methyl ester (60 mg, 0.47 mmol), and the reaction was stirred at rt overnight. The solution was then poured onto a silica column eluting with 100% EtOAc to yield compound C as a white solid (100 mg, 75%).

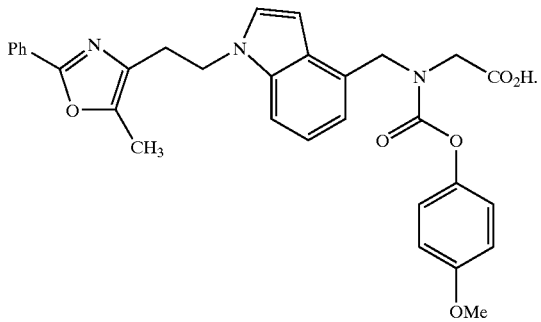

Compound C (20 mg, 0.048 mmol) and 4-methoxyphenyl chloroformate (14 mg, 0.72 mmol) were dissolved in 1 ml CH$_2$Cl$_2$, then Et$_3$N was added and the reaction was stirred at rt for 15 min. The aqueous phase was washed with NH$_4$Cl (2×2 mL), dried with Na$_2$SO$_4$, and then evaporated in vacuo. The residue was then dissolved in 10:1 MeOH:H$_2$O (2 mL), treated with LiOH (15 mg, 0.75 mmol), and the reaction was stirred at rt for 2 h. Volatiles were removed in vacuo and the residue was acidified to pH 2 with aqueous 1 M HCl, then extracted with EtOAc (3×2 mL). The combined organic extracts were dried (Na$_2$SO$_4$) and then concentrated in vacuo. The crude product was purified by preparative HPLC (YMC 5 ODS 50×250 mm column; flow rate=25 mL/min; continuous 20 min gradient from 70:30 B:A to 100% B, where A=90:10:0.1 H$_2$O:MeOH:TFA and B=90:10:0.1 MeOH:H$_2$O:TFA) to afford title compound (8.8 mg, 23% in two steps) as a colorless oil. [M+H$^+$]=540.2

$^1$H NMR (400 MHz, CDCl$_3$) Rotamers δ 1.58/1.63 (s, 3H), 2.98/2.92 (t, J=4 Hz, 2H), 3.77/3.79 (s, 3H), 4.04/4.07 (s, 2H), 4.18/4.34 (t, J=8 Hz, 2H), 4.73/4.83 (s, 2H), 6.375/6.405 (d, J=4 Hz, 1H), 6.84–6.92 (m, 3H), 7.04–7.27 (m, 3H), 7.43–7.53 (m, 4H), 7.95–7.98 (m, 2H), 10.80 (br. s, 1H).

EXAMPLES 10 TO 16

The following compounds were prepared in a manner analogous to Example 9:

EXAMPLE 10

[M+H$^+$]=524.3

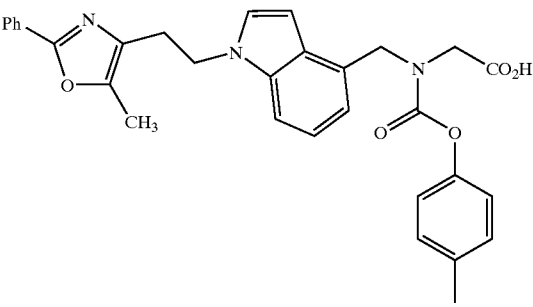

EXAMPLE 11

[M+H$^+$]=554.2

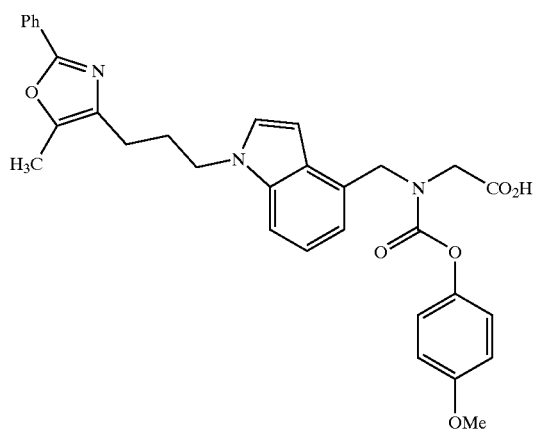

EXAMPLE 12

[M+H$^+$]=538.2

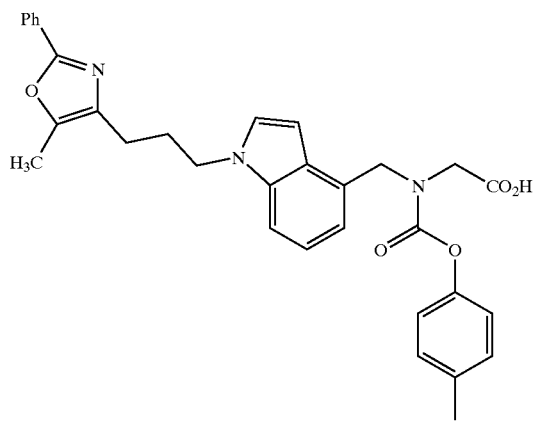

EXAMPLE 13

[M+H$^+$]=538.2

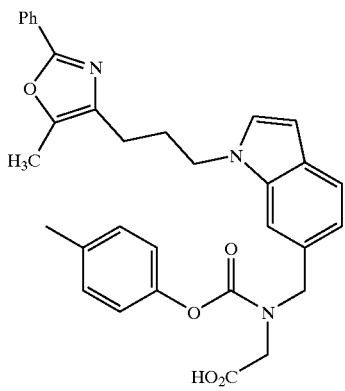

EXAMPLE 14

[M+H$^+$]=554.2

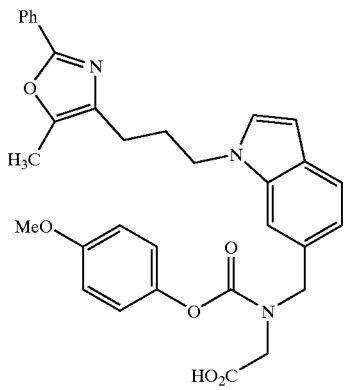

EXAMPLE 15

[M+H$^+$]=524.4

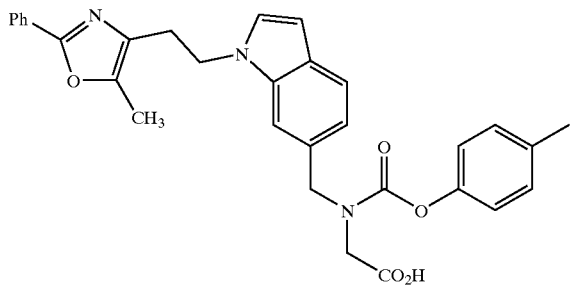

EXAMPLE 16

[M+H$^+$]=540.3

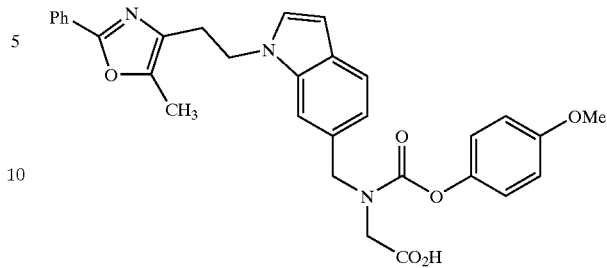

What is claimed is:
1. A compound which has the structure

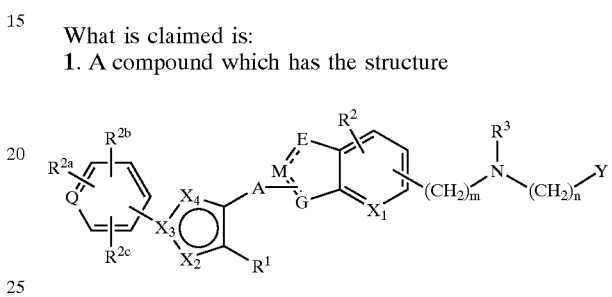

wherein m is 0, 1 or 2; n=0, 1 or 2;

Q is C

A is $(CH_2)_x$ where x is 1 to 5; or A is $(CH_2)_x{}^1$, where $x^1$ is 2 to 5, with an alkenyl bond or an alkynyl bond embedded in the chain; or A is $—(CH_2)_x{}^2—O—(CH_2)_x{}^3—$ where $x^2$ is 0 to 5 and $x^3$ is 0 to 5, provided that at least one of $x^2$ and $x^3$ is other than 0, $X_1$ is CH $X_2$ is O or S;

$X_3$ is $CR^e$;

$X_4$ is $NR^f$, wherein $R^e$ selected from a single bond, H, alkyl, alkoxy, aryl, cycloalkyl, amino or substituted amino, and $R^f$ selected from a single bond, H, alkyl, aryl, heteroaryl, cycloalkyl or cycloheteroalkyl, provided that at least one of $X_2$, $X_3$ and $X_4$ is $$—\overset{|}{N}—;$$

E is $NR^g$;

M is $R^j$;

G is O or S, wherein $R^g$ is selected from a single bond, H, alkyl, aryl, cycloalkyl, heteroaryl or cycloheteroalkyl; and $R^j$ is selected from a single bond, H, alkyl, alkoxy, aryl, cycloalkyl, amino or substituted amino, provided where in each of $X_1$ through $X_4$ as defined above, C may include CH;

$R^1$ is H or alkyl;

$R^2$ is H, alkyl, alkoxy, halogen, amino or substituted amino;

$R^{2a}$, $R^{2b}$ and $R^{2c}$ are the same or different and are selected from H, alkyl, alkoxy, halogen, amino or substituted amino;

$R^3$ is selected from aryloxycarbonyl, alkyloxycarbonyl, alkynyloxycarbonyl, alkenyloxycarbonyl, alkyl(halo)aryloxycarbonyl, alkyloxy(halo)aryloxycarbonyl, cycloalkylaryloxycarbonyl, cycloalkyloxyaryloxycarbonyl, alkylcarbonylamino, arylcarbonylamino, heteroarylcarbonylamino, alkoxycarbonylamino, aryloxycarbonylamino, heteroaryloxycarbonylamino, alkylsulfonyl, alkenylsulfonyl, heteroaryloxycarbonyl, cycloheteroalkyloxycarbonyl, heteroarylalkenyl, hydroxyalkyl, alkoxy, alkoxyaryloxycarbonyl, arylalkyloxycarbonyl, alkylaryloxycarbonyl, haloalkoxyaryloxycarbonyl, alkoxycarbonylaryloxycarbonyl, aryloxyaryloxycarbonyl, heteroaryloxyarylalkyl, aryloxyarylalkyloxycarbonyl, arylalkenyloxycarbonyl, aryloxyalkyloxycarbonyl, arylalkylsulfonyl, arylthiocarbonyl, arylalkenylsulfonyl, heteroarylsulfonyl, arylsulfonyl, heteroarylalkoxycarbonyl, heteroarylalkyloxyarylalkyl, arylalkenylarylalkyl, heteroaryloxyarylalkyl, arylalkenylheteroarylalkyl, or polyhaloalkylaryloxycarbonyl;

Y is $CO_2R^4$ (where $R^4$ is H or alkyl, or a prodrug ester) or Y is a C-linked 1-tetrazole, a phosphinic acid of the structure $P(O)(OR^{4a})R^5$ ($R^5$ is alkyl or aryl, or a phosphonic acid of the structure $P(O)(OR^{4a})_2$ (where $R^{4a}$ is H or a prodrug ester);

$(CH_2)_x$, $(CH_2)_x^1$, $(CH_2)_x^2$, $(CH_2)_x^3$, $(CH_2)_m$, and $(CH_2)_n$ may be optionally substituted with 1, 2 or 3 substituents;

stereoisomers thereof, a prodrug ester thereof, and a pharmaceutically acceptable salt thereof.

2. A compound having the structure

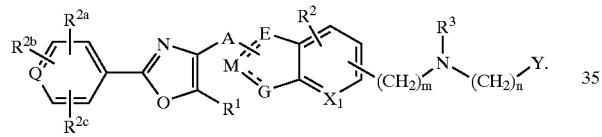

wherein $R^{2a}$, $R^{2b}$, $R^{2c}$, Q, A, $R^1$, E, M, G, $X_1$, $R^2$, m, $R^3$, n and y are as defined in claim 1.

3. The compound as defined in claim 1 having the structure

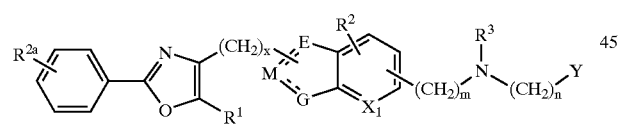

4. The compound as defined in claim 1 having structure

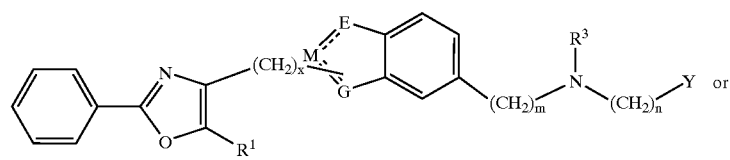

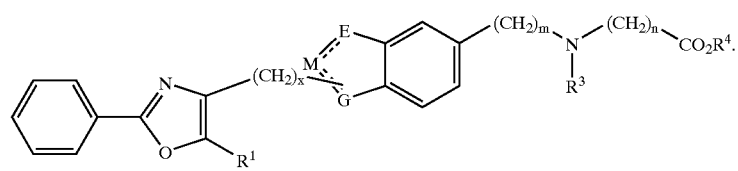

5. The compound as defined in claim 1 wherein $(CH_2)_x$, $(CH_2)_x^1$, $(CH_2)_x^2$, $(CH_2)_x^3$ are alkylene, alkenylene, allenyl, or alkynylene.

6. The compound as defined in claim 1 wherein $X_1$ is CH.

7. The compound as defined in claim 1 wherein M is C.

8. The compound as defined in claim 1 wherein M is C, E is N or C, and G is O or N.

9. The compound as defined in claim 1 wherein m is 1 and x is 1, 2 or 3.

10. The compound as defined in claim 1 wherein

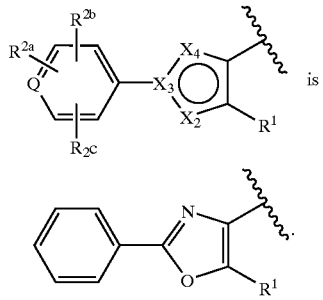 is

11. The compound as defined in claim 1 wherein $R^3$ is

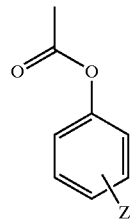

wherein Z is alkoxy, alkyl or halo.

12. The compound as defined in claim 1 wherein Y is $CO_2R^4$.

13. The compound as defined in claim 1 wherein

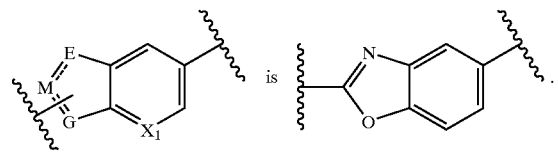

14. The compound as defined in claim 1 having the structure

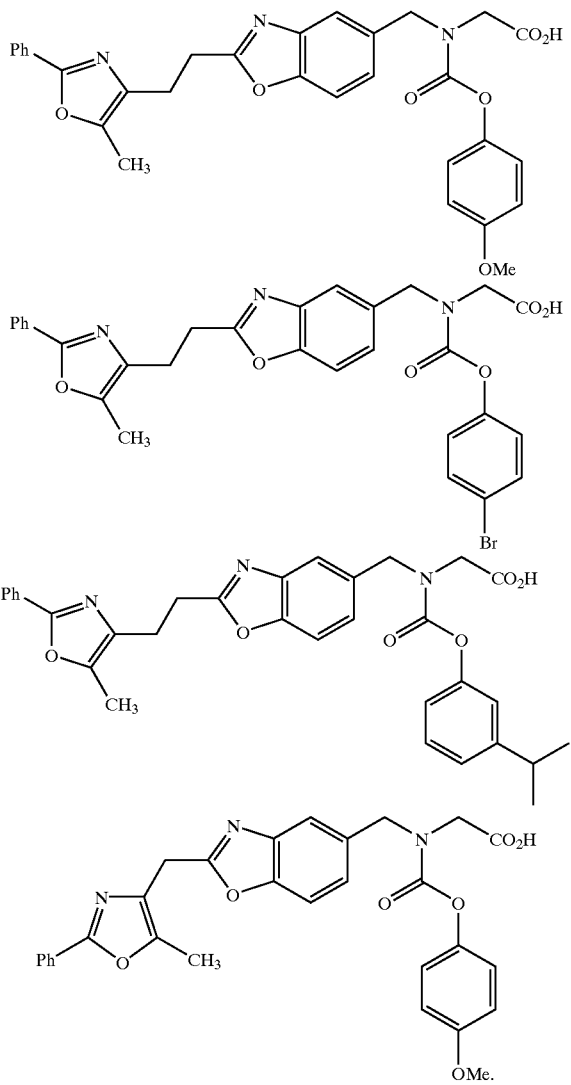

15. A pharmaceutical composition comprising a compound as defined in claim 1 and a pharmaceutically acceptable carrier therefor.

16. A method for lowering blood glucose levels which comprises administering to a patient in need of treatment a therapeutically effective amount of a compound as defined in claim 1.

17. A method for treating diabetes which comprises administering to a patient in need of treatment a therapeutically effective amount of a compound as defined in claim 1.

18. A pharmaceutical combination comprising a compound as defined in claim 1 and a lipid-lowering agent, a lipid modulating agent, an antidiabetic agent, an anti-obesity agent, an antihypertensive agent, a platelet aggregation inhibitor, and/or an antiosteoporosis agent.

19. The pharmaceutical combination as defined in claim 18, comprising said compound and an antidiabetic agent.

20. The combination as defined in claim 19 wherein the antidiabetic agent is selected from 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide.

21. The combination as defined in claim 20 wherein the antidiabetic agent is selected from 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, P32/98 and/or NVP-DPP-728A.

22. The combination as defined in claim 19 wherein the compound is present in a weight ratio to the antidiabetic agent within the range from about 0.001 to about 100:1.

23. The combination as defined in claim 18 wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent.

24. The combination as defined in claim 23 wherein the anti-obesity agent is orlistat, ATL-962, AJ9677, L750355, CP331648, sibutramine, topiramate, axokine, dexamphetamine, phentermine, phenylpropanolamine, and/or mazindol.

25. The combination as defined in claim 18 wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor.

26. The combination as defined in claim 25 wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427.

27. The combination as defined in claim 25 wherein the compound is present in a weight ratio to the lipid-lowering agent within the range from about 0.001:1 to about 100:1.

28. The combination as defined in claim 18 wherein the antihypertensive agent is an ACE inhibitor, angiotensin II receptor antagonist, NEP/ACE inhibitor, calcium channel blocker and/or β-adrenergic blocker.

29. The combination as defined in claim 28 wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat), CGS 30440 or MD 100240;

an angiotensin II receptor antagonist which is irbesartan, losartan or valsartan;

amlodipine besylate, prazosin HCl, verapamil, nifedipine, nadolol, propranolol, carvedilol, or clonidine HCl.

30. The combination as defined in claim 18 wherein the platelet aggregation inhibitor is aspirin, clopidogrel, ticlopidine, dipyridamole or ifetroban.

31. A method for treating insulin resistance, hyperglycemia, hyperinsulinemia, or elevated blood levels of free fatty acids or glycerol, hyperlipidemia, obesity, Syndrome X, dysmetabolic syndrome, inflammation, diabetic complications, impaired glucose homeostasis, impaired glucose tolerance, hypertriglyceridemia or atherosclerosis which comprises administering to a mammalian species in need of treatment a therapeutically effective amount of a pharmaceutical combination as defined in claim 19.

32. The method of treating a malignant disease, wherein the disease is a liposarcoma or an epithelial tumor.

33. The method as defined in claim 32 wherein the epithelial tumor is a tumor of the breast, prostate, colon, ovaries, stomach or lung.

34. The method of treating a malignant disease, wherein the disease is ductal carcinoma in situ of the breast, lobular carcinoma in situ of the breast, fibroadenoma of the breast, or prostatic intraepithelial neoplasia.

35. A method for treating irritable bowel syndrome, Crohn's disease, gastric ulceritis or osteroporosis, or psoriasis, which comprises administering to a mammalian species in need of treatment a therapeutically effective amount of a compound as defined in claim 1.

* * * * *